United States Patent [19]

Seto et al.

[11] Patent Number: 4,559,297
[45] Date of Patent: Dec. 17, 1985

[54] SILVER HALIDE COLOR PHOTOGRAPHIC LIGHT-SENSITIVE MATERIAL CONTAINING STABILIZER

[75] Inventors: Nobuo Seto; Nobuo Furutachi; Masakazu Morigaki; Kiyoshi Nakazyo, all of Kanagawa, Japan

[73] Assignee: Fuji Photo Film Co., Ltd., Kanagawa, Japan

[21] Appl. No.: 699,091

[22] Filed: Feb. 7, 1985

[30] Foreign Application Priority Data

Feb. 7, 1984 [JP] Japan .................................. 59-20538
Sep. 6, 1984 [JP] Japan ................................. 59-186857

[51] Int. Cl.$^4$ ............................................. G03C 7/26
[52] U.S. Cl. ................................. 430/551; 430/558; 430/607
[58] Field of Search ................. 430/551, 558, 607, 372

[56] References Cited

U.S. PATENT DOCUMENTS

| | | | |
|---|---|---|---|
| 4,264,720 | 4/1981 | Hamaoka et al. | 430/551 |
| 4,266,020 | 5/1981 | Sakai et al. | 430/551 |
| 4,279,990 | 7/1981 | Aoki et al. | 430/372 |
| 4,283,488 | 8/1981 | Van Lare | 430/588 |
| 4,332,886 | 6/1982 | Aoki et al. | 430/372 |
| 4,500,630 | 2/1985 | Sato et al. | 430/558 |

*Primary Examiner*—J. Travis Brown
*Attorney, Agent, or Firm*—Sughrue, Mion, Zinn, Macpeak, and Seas

[57] ABSTRACT

A silver halide photographic light-sensitive material is described, the material comprising a support having thereon at least one photographic layer containing at least one compound represented by formula (I):

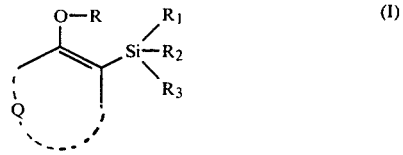

wherein R represents a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group,

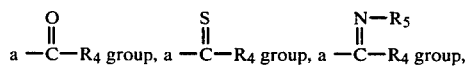

a substituted or unsubstituted silyl group, a substituted or unsubstituted phosphoric acid group, or a divalent group derived from the above-described groups which forms a ring together with the oxygen atom linking to —R and the carbon atom which is in the ortho-position to —O—R and to which

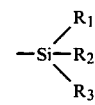

is not bonded; $R_1$, $R_2$ and $R_3$ which may be the same or different each represents a hydrogen atom, an alkyl group, an alkenyl group, a cycloalkyl group, an aralkyl group, an aryl group or a substituent thereof; Q represents an atomic group necessary to form a substituted or unsubstituted aromatic ring; $R_4$ represents a hydrogen atom, an alkyl group, a cycloalkyl group, an alkenyl group, an aryl group, an alkoxy group, an aryloxy group, an amino group, a cycloamino group, an alkylthio group, an arylthio group, an acyl group, an alkoxycarbonyl group or a substituent thereof; and $R_5$ represents an H atom, an alkyl group, a cycloalkyl group, an alkenyl group, an aryl group or a substituent thereof.

19 Claims, No Drawings

SILVER HALIDE COLOR PHOTOGRAPHIC LIGHT-SENSITIVE MATERIAL CONTAINING STABILIZER

FIELD OF THE INVENTION

This invention relates to a silver halide color photographic light-sensitive material, and more particularly, to a silver halide color photographic light-sensitive material having reduced decoloration of images and reduced discoloration of non-image areas.

BACKGROUND OF THE INVENTION

Generally speaking, photographic images obtained from silver halide photographic light-sensitive materials are not permanent and gradually deteriorate with the passage of time. In particular, color images formed by azomethine dyes or indoaniline dyes produced by the reaction between an oxidation product of an aromatic primary amine developing agent and a coupler, when exposed to light for a long time or preserved in a high temperature and high humidity atmosphere, usually undergo decoloration or discoloration of image areas and also discoloration of the non-image areas, i.e., white background, resulting in deterioration of image quality.

Such deterioration of image quality is a serious defect for recording materials. Various compounds have been proposed in order to overcome this problem, but none of them has succeeded in producing the desired effect.

For example, conventionally known compounds which have been used for preventing decoloration or discoloration of color images include hydroquinone derivatives, e.g., 2,5-di-t-butylhydroquinone as is described in U.S. Pat. Nos. 2,360,290, 2,418,613, 2,700,453, 2,701,197, 2,728,659, 2,732,300, 2,735,765, 3,982,944, 4,430,425, 2,710,801 and 2,816,028; phenol compounds, e.g., 2,6-di-t-butyl-p-cresol, 4,4′-methylenebis(2,6-di-t-butylphenol), 2,2′-methylenebis(4-ethyl-6-t-butylphenol) or 4,4′-isopropylidenediphenol as is described in U.S. Pat. Nos. 2,735,765, 3,700,455 and 4,228,235; British Pat. No. 2,066,975; Japanese Patent Publication Nos. 19764/82 and 6623/77 and Japanese Patent Application (OPI) No. 10539/84; compounds obtained by substituting a hydroxyl group of couroman derivatives such as tocopherols or dihydroxyindane derivatives as is described in U.S. Pat. Nos. 3,432,300, 3,573,050, 3,574,627, 3,698,909, 3,764,337 and Japanese Patent Application (OPI) No. 15222/77 with an alkoxy group, an acyloxy group or a silyl group; and methylenedioxybenzene derivatives and aminophenols as is described in U.S. Pat. Nos. 3,457,079 and 4,332,886, and Japanese Patent publication No. 21144/81. However, some of these compounds fail to produce the desired effect although a certain effect may be achieved; or some of them have adverse effects, such as deterioration in hue, generation of fog, poor dispersion, crystallization, and the like, despite their effect of preventing decoloration. Therefore, they are unsatisfactory as color image stabilizers having synthetically excellent effects.

SUMMARY OF THE INVENTION

Accordingly, an object of this invention is to provide a silver halide photographic light-sensitive material which contains an image stabilizer for preventing deterioration of image quality with the passage of time.

Another object of this invention is to provide a silver halide photographic light-sensitive material which can provide a stabilized color image by incorporating a stabilizer which sufficiently prevents decoloration or discoloration of a color image without causing a change in hue or generating fog.

A further object of this invention is to provide a silver halide photographic light-sensitive material containing the above-described stabilizer in the photographic layer thereof, by which the unexposed area of the light-sensitive material after development processing is free from yellow stain due to exposure to light, heat or humidity.

As a result of extensive studies, it has now been found that these objects can be accomplished by incorporating at least one of the compounds represented by the following formula (I) in a photographic layer.

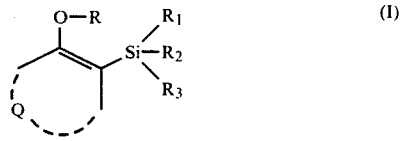

wherein R represents a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group,

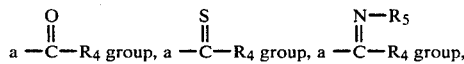

a substituted or unsubstituted silyl group, a substituted or unsubstituted phosphoric acid group, or a divalent group derived from the above-described groups which forms a ring together with the oxygen atom linking to —R and the carbon atom which is in the ortho-position to —O—R and to which

is not bonded; $R_1$, $R_2$ and $R_3$ which may be the same or different each represents a hydrogen atom, a substituted or unsubstituted alkyl group, a substituted or unsubstituted alkenyl group, a substituted or unsubstituted cycloalkyl group, or a substituted or unsubstituted aryl group; Q represents an atomic group necessary to form a substituted or unsubstituted aromatic ring; $R_4$ represents a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted alkoxy group, a substituted or unsubstituted aryloxy group, a substituted or unsubstituted amino group, a substituted or unsubstituted cycloamino group, a substituted or unsubstituted alkylthio group, a substituted or unsubstituted arylthio group, a substituted or unsubstituted acyl group, or a substituted or unsubstituted alkoxycarbonyl group; and $R_5$ represents a substituted or unsubstituted alkyl group, a substituted or unsubstituted cycloalkyl group, a substituted or unsubstituted alkenyl group, or a substituted or unsubstituted aryl group.

DETAILED DESCRIPTION OF THE INVENTION

In the above-described formula (I), R represents a hydrogen atom, a straight or branched chain, substituted or unsubstituted alkyl group (e.g., a methyl group, an ethyl group, an octyl group, a 2-ethylhexyl group or a dodecyl group), a substituted or unsubstituted alkenyl group (e.g., an allyl group), a substituted or unsubstituted cycloalkyl group (e.g., a cyclopentyl group or a cyclohexyl group), a substituted or unsubstituted aryl group (e.g., a phenyl group or a naphthyl group), a substituted or unsubstituted 5- to 7-membered heterocyclic ring containing at least one of, e.g., an oxygen atom, a nitrogen atom or a sulfur atom as a hetero atom (e.g., a 1-piperidino group, a 2-furyl group, a 2-thiophenyl group or a 2-benzothiazolyl group),

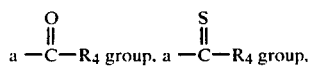

wherein $R_4$ represents a hydrogen atom, the same alkyl, cycloalkyl, alkenyl or aryl group as defined for R, a substituted or unsubstituted alkoxy group (e.g., a methoxy group, a butoxy group, a 2-chloroethoxy group, a methoxyethoxy group, a 2-ethylhexyloxy group or a benzyloxy group), a substituted or unsubstituted aryloxy group (e.g., a phenoxy group, a 2,4-dichlorophenoxy group or a 4-t-octylphenoxy group), a substituted or unsubstituted amino group (e.g., an amino group, an N,N-diethylamino group, an N-dodecylamino group, a cyclohexylamino group, an anilino group, a 2-chloroanilino group or a 2-methoxyanilino group), a substituted or unsubstituted cycloamino group (e.g., a piperidino group or a morpholino group), a substituted or unsubstituted alkylthio group (e.g., a butylthio group or a dodecylthio group), a substituted or unsubstituted arylthio group (e.g., a phenylthio group, a 4-dodecylphenylthio group or a 4-t-butylphenylthio group), a substituted or unsubstituted acyl group (e.g., an acetyl group, a benzoyl group or a phenylacetyl group), or a substituted or unsubstituted alkoxycarbonyl group (e.g., an ethoxycarbonyl group, a dodecyloxycarbonyl group, etc.),

group, wherein $R_5$ represents a hydrogen atom, a substituted or unsubstituted alkyl group (e.g., a methyl group, an ethyl group or a t-butyl group), a substituted or unsubstituted cycloalkyl group (e.g., a cyclohexyl group), a substituted or unsubstituted alkenyl group, or a substituted or unsubstituted aryl group (e.g., a phenyl group or a 2-chlorophenyl group), a substituted or unsubstituted silyl group of the formula

(hereinafter defined), a phosphoric acid group of the formula

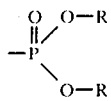

wherein R is as defined above, or a divalent group derived from the above-described groups for R which forms a ring together with the oxygen atom linking to —R and the carbon atom which is in the ortho-position to —O—R and to which

is not bonded (e.g., —CH$_2$O—,

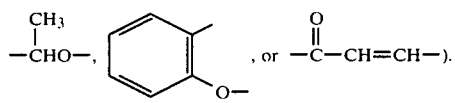

Examples of the substituents for the substituted alkyl, alkenyl, cycloalkyl, aryl and heterocyclic group as represented by R include a halogen atom, a cyano group, a hydroxyl group, a mercapto group, a carboxyl group, a sulfoxy group, a nitro group, a carbamoyl group, an alkoxycarbonyl group, an aryloxycarbonyl group, an acyl group, an aryl group, an acyloxy group, an alkoxycarbonyloxy group, an aryloxy group, a heterocyclic oxy group, an alkoxy group, a silyloxy group, a sulfonyloxy group, a carbamoyloxy group, an acylamino group, a sulfonamido group, an alkoxycarbonylamino group, an aryloxycarbonylamino group, an imido group, an amino group (e.g., an N-alkylamino group, an N,N-dialkylamino group, an N-arylamino group or an N-heterocyclic amino group), a ureido group, a sulfamoyl group, an alkylsulfonyl group, an arylsulfonyl group, an alkylsulfinyl group, an arylsulfinyl group, an alkylthio group, an arylthio group, a heterocyclic group (e.g., a 5- to 7-membered ring containing at least one of a hetero atom such as an oxygen atom, a nitrogen atom and a sulfur atom.

$R_1$, $R_2$ and $R_3$ each represents a hydrogen atom, a substituted or unsubstituted alkyl group (e.g., a methyl group, a propyl group, a t-butyl group or an octyl group), a substituted or unsubstituted alkenyl group (e.g., an allyl group), a substituted or unsubstituted cycloalkyl group (e.g., a cyclopentyl group or a cyclohexyl group), a substituted or unsubstituted aralkyl group (e.g., benzyl group), or a substituted or unsubstituted aryl group (e.g., a phenyl group, a 4-methylphenyl group or a 4-t-octylphenyl group).

Q represents an atomic group necessary to form a substituted or unsubstituted aromatic ring.

Among the compounds represented by formula (I), preferred compounds are represented by the following formulae (II) to (IX). In these formulae, R, $R_1$, $R_2$ and $R_3$ are as defined above; $R_6$ represents the same group as defined for R, provided that R and $R_6$ may be the same or different; and $R_7$ and $R_8$ each represents a hydrogen atom, or the same alkyl or aryl group as defined for R. Further, in these formulae (II)–(IX), the carbon atoms that are not specified by $R_1$ to $R_8$ may be substituted by a halogen atom, an alkyl group, an aryl group or a

group which are defined for R.
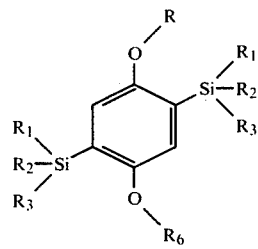 (II)
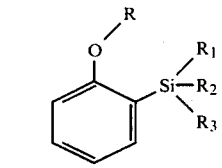 (III)
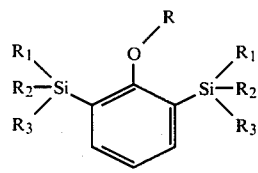 (IV)
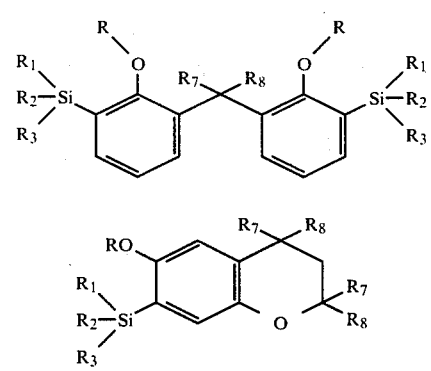 (V)
(VI)
(VI)
(VII)
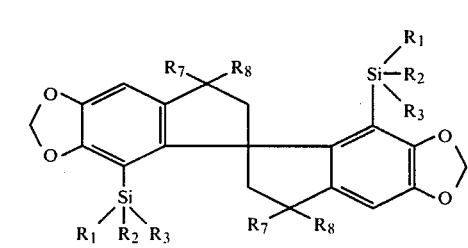 (VIII)
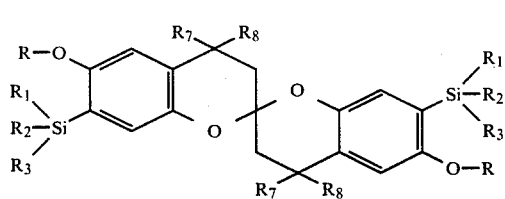 (IX)
Specific examples of the compounds represented by the formula (I) which can be used in the present invention are shown below, but the present invention is not limited thereto.
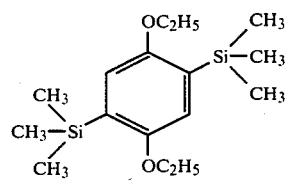 1.
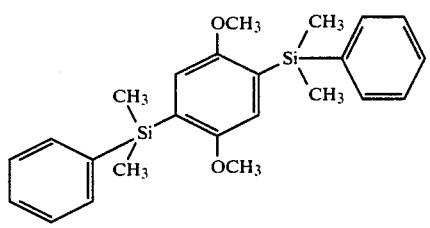 2.
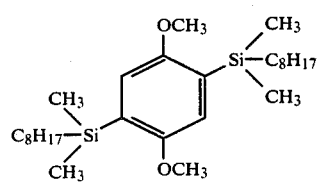 3.
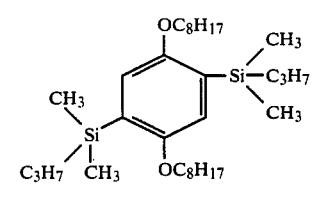 4.
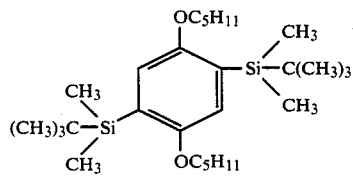 5.

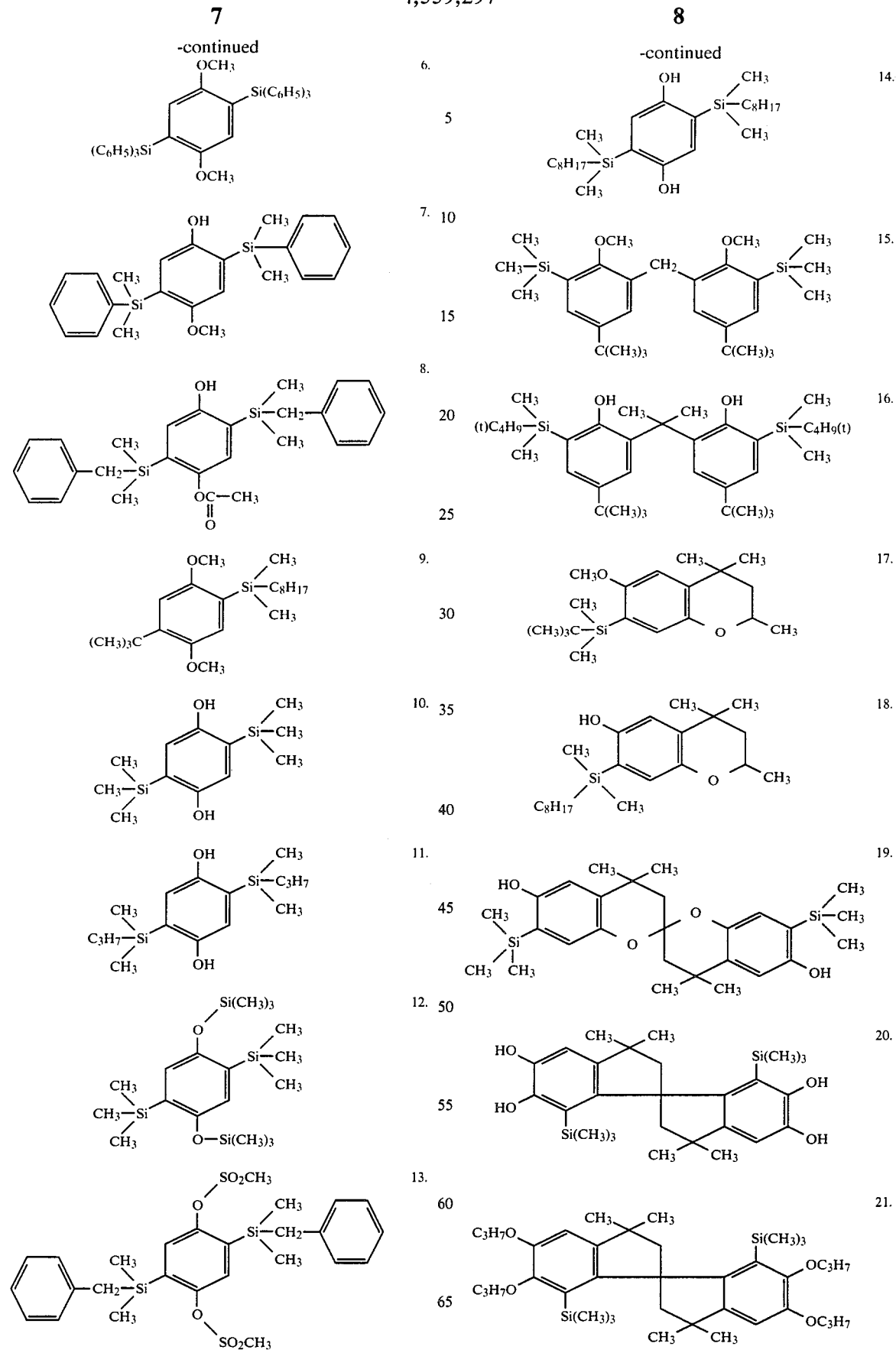

-continued

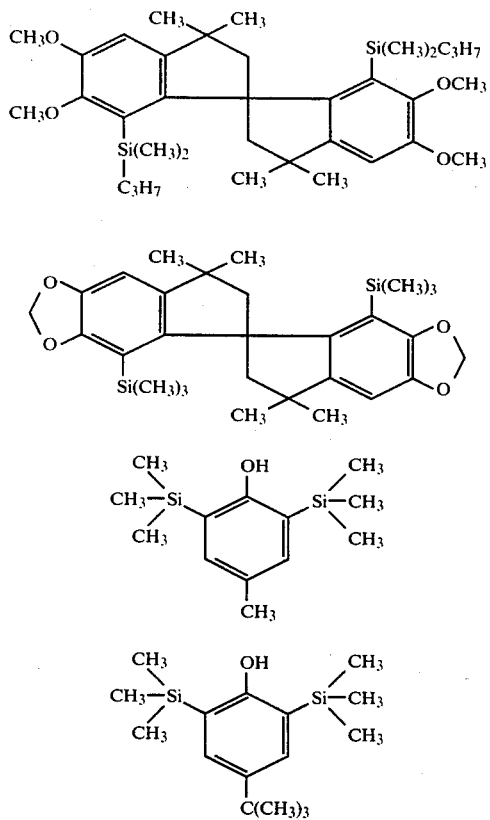

22.

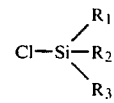

These aryl tri-substituted silane compounds can be synthesized by the process specifically described in Synthesis Review, 841 (1979). However, the inventors have found that the compounds of the formula (I) can conveniently and advantageously be synthesized by the following process:

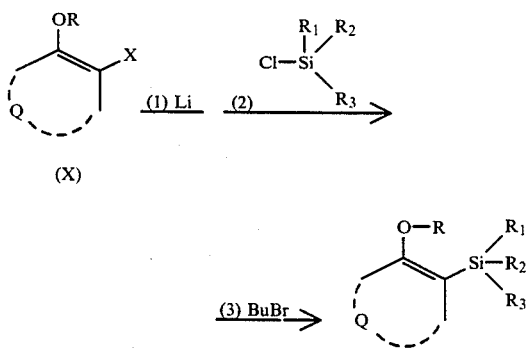

wherein R represents an alkyl group; and X represents a halogen atom.

More specifically, the starting compound represented by the formula (X) is dissolved in a dried ether solvent, e.g., diethyl ether, tetrahydrofuran or dioxane, and an amount of metallic lithium equal to 2 to 4 times the molar amount of compound (X) is added to the solution at a temperature of from −78° C. to 70° C. An amount of equal to double the molar amount of compound (X) is added thereto, and the mixture is thoroughly stirred. Then, an amount of butyl bromide equal to 0.2 to 2 times the molar amount of compound (X) is added thereto dropwise, followed by thoroughly stirring. The reaction proceeds at a rate as high as 60% or more to produce the compound of formula (I).

Dealkylation of the compound of formula (I) can be carried out in accordance with a well-known method, as described in, e.g., T. W. Greene, *Protective Groups in Organic Synthesis*, John Wiley & Sons (1981).

Among the compounds of the formula (I), those having a silyl group introduced on the phenyl nucleus of hydroquinone can be synthesized by the following process to advantage:

Process B:

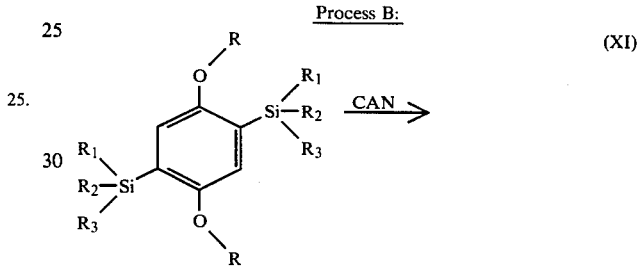

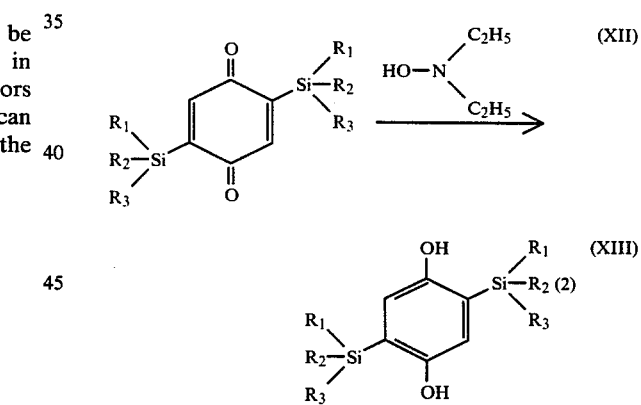

where R is an alkyl group, and $R_1$, $R_2$ and $R_3$ are as defined above; and CAN represents ceric (IV) ammonium nitrate.

More specifically, the hydroquinone diether compound represented by formula (XI) which can be obtained through Process A is converted to the quinone compound represented by the formula (XII) using ceric (IV) ammonium nitrate in accordance with the method described in *J. Org. Chem.*, 46, 2749 (1981). Compound (XII) can easily be converted to the desired compound of the formula (XIII) using N,N-diethylhydroxylamine by the method described in *J. Org. Chem.* 44, 2647 (1979).

Synthesis examples of typical compounds of formula (I) are shown below, although the present invention is not to be construed as being limited thereto. Other compounds can also be synthesized in a similar manner.

SYNTHESIS EXAMPLE 1

Synthesis of 2,5-Bis(Trimethylsilyl)Hydroquinone Diethyl Ether (Compound No. 1)

To 32.4 g (0.1 mol) of 2,5-dibromohydroquinone diethyl ether were successively added 160 ml of diether ether, 2.8 g (0.4 gram-atom) of metallic lithium and 21.7 g (0.2 mol) of trimethylsilyl chloride, and the mixture was stirred under a nitrogen stream at 20° to 23° C. 27.4 g (0.2 mol) of butyl bromide was added dropwise to the mixture over a period of 1 hour, and the stirring was continued for an additional one hour while heating at 35° C. After cooling with ice, 50 ml of methanol was added thereto, followed by stirring. The reaction mixture was poured into water, and was extracted with 200 ml of ethyl acetate. The ethyl acetate layer was washed with 200 ml of a saturated aqueous solution of sodium chloride, and dried over anhydrous sodium sulfate. After filtration, the filtrate was concentrated to dryness and crystallized from acetonitrile. Recrystallization from acetonitrile gave 15.5 g (yield: 50%) of 2,5-bis(-trimethylsilyl)hydroquinone diethyl ether having a melting point of 129° C.

Elementary Analysis: Calc. (%): H 9.74%; C 61.88%; Found (%): H 9.97%; C 61.92%

SYNTHESIS EXAMPLE 2

Synthesis of 2,5-Bis(Dimethyloctylsilyl)Hydroquinone Dimethyl Ether (Compound No. 3)

To 27.3 g (0.092 mol) of 2,5-dibromohydroquinone dimethyl ether were successively added 140 ml of tetrahydrofuran, 2.6 g (0.371 gram-atom) of metallic lithium and 38 g (0.184 mol) of dimethyloctylsilyl chloride, and the mixture was stirred in a nitrogen stream at 20° to 23° C.

27.4 g (0.20 mol) of butyl bromide was added dropwise thereto over a period of 1 hour, and the stirring was continued for an additional one hour while heating to 50° C. The reaction mixture was cooled with ice, and 50 ml of methanol was added thereto, followed by stirring. The reaction mixture was poured into water, and was extracted with 200 ml of ethyl acetate was added. The ethyl acetate layer was washed with 200 ml of a saturated aqueous solution of sodium chloride, and dried over anhydrous sodium sulfate. The sodium sulfate was separated by filtration, and the filtrate was concentrated and distilled under reduced pressure to obtain 21 g (yield: 47%) of 2,5-bis(dimethyloctylsilyl)hydroquinone dimethyl ether as an oily substance (boiling point: 170° C./0.1 mmHg).

Elementary Analysis: Calc. (%): H 11.37%; C 70.22%; Found (%): H 11.64%; C 71.12%

SYNTHESIS EXAMPLE 3

Synthesis of 2,5-Bis(Trimethylsilyl)Hydroquinone (Compound No. 10)

(a) Synthesis of 2,5-Bis(Trimethylsilyl)Benzoquinone (Intermediate No. 1)

13.7 g (0.025 mol) of ceric (IV) ammonium nitrate was dissolved in 20 ml of water, and the solution was stirred at 25° C. To the resulting solution was slowly added a solution prepared by dissolving 3.1 g (0.01 mol) of 2,5-bis(trimethylsilyl)hydroquinone diethyl ether as prepared in Synthesis Example 1 in 50 ml of acetonitrile while heating to 50° C., followed by stirring for 30 minutes. The reaction mixture was poured into 100 ml of ice-water. The precipitated crystals were filtered, washed with water and recrystallized from acetonitrile to obtain 2.1 g (yield: 83%) of crystals 2,5-bis(trimethylsilyl)benzoquinone having a melting point of 180° C.

(b) Synthesis of 2,5-Bis(trimethylsilyl)Hydroquinone

To 2.1 g (8.3 mmol) of 2,5-bis(trimethylsilyl)benzoquinone (Intermediate No. 1) were added 20 ml of ethyl acetate and 1.1 g (12.5 mmol) of N,N-diethylhydroxylamine, and the mixture was heated under reflux for 30 minutes. The reaction mixture was concentrated under reduced pressure to dryness, and the solid was crystallized from acetonitrile. The crystals were collected by filtration and recrystallized from acetonitrile to yield 1.7 g (yield: 80%) of crystals of 2,5-bis(trimethylsilyl)hydroquinone having a melting point of 162° C.

Elementary Analysis: Calc. (%): H 8.71%; C 56.64%; Found (%): H 8.87%; C 56.43%

The compounds for formula (I) according to the present invention may be employed as stabilizers for achromatic photographic light-sensitive materials, but are particularly useful as color image stabilizers for color photographic light-sensitive materials.

Silver halide color photographic light-sensitive materials generally comprise a support having provided thereon at least one red-sensitive emulsion layer, at least one green-sensitive emulsion layer, and at least one blue-sensitive emulsion layer in an arbitrarily selected order. It is usual to incorporate a cyan forming coupler into a red-sensitive emulsion layer; a magenta forming coupler in a green-sensitive emulsion layer; and a yellow forming coupler in a blue-sensitive emulsion layer, respectively, but other combinations may also be used, if desired.

The silver halide color photographic light-sensitive material includes color negative films, color positive films, color reversal films, color photographic papers, color reversal photographic papers, and the like.

The present invention can be applied not only to the above-described panchromatic light-sensitive materials but also to monochromatic light-sensitive materials and color light-sensitive materials which provide a silver image and a dye image simultaneously.

The compounds represented by the formula (I) according to the present invention can be incorporated in a photographic layer including a silver halide light-sensitive emulsion layer, such as a silver halide achromatic light-sensitive emulsion layer, a red-sensitive silver halide emulsion layer, a green-sensitive silver halide emulsion layer, and a blue-sensitive silver halide emulsion layer; and a light-insensitive photographic auxiliary layer, such as an intermediate layer, an overcoat layer, a subbing layer, a filter layer, an antihalation layer, or a backing layer. The compounds (I), when incorporated in an intermediate layer, prevent color turbidity; and, when incorporated in a dye forming coupler-containing photographic layer, stabilize a dye image. They are particularly effective for prevention of decoloration or discoloration of a magenta image when incorporated in a magenta coupler-containing photographic layer.

The compound (I) of the present invention can be used in an amount of from about $1 \times 10^{-5}$ to 1 mol, and preferably from about $1 \times 10^{-3}$ to $5 \times 10^{-1}$ mol, per mol of silver halide. When the compound (I) is incorporated into the light-insensitive layer, it is used in an amount of from about $3 \times 10^{-6}$ to $3 \times 10^{-1}$ mol/m$^2$, preferably from about $3 \times 10^{-3}$ to $1.5 \times 10^{-1}$ mol/m$^2$.

In the photographic emulsion layers of photographic materials prepared in accordance with the present invention, conventional color forming couplers, i.e., compounds capable of forming colors upon coupling with an oxidation product of aromatic primary amine developers in color development processing, can be used in combination with the compounds of formula (I).

These couplers desirably are rendered nondiffusible by hydrophobic groups called ballast groups in their molecules. These couplers may be either 4-equivalent or 2-equivalent with respect to silver ions.

Further, the photographic emulsion layer of the photographic material according to the present invention may contain colored couplers having a color correcting effect, or the so-called DIR couplers capable of releasing development inhibitors with the progress of development. In addition to the DIR couplers, colorless DIR coupling compounds which produce colorless products upon coupling may also be used.

Yellow forming couplers can be used in the present invention include known open-chain keto methylene couplers. Of these, benzoylacetoanilide compounds and pivaloylacetoanilide compounds are advantageous. Specific examples of the yellow couplers are described in, e.g., U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77 (the term "OPI" herein used refers to a "published unexamined Japanese patent application").

Magenta forming couplers which can be used in the present invention include pyrazolone compounds, indazolone compounds, cyanoacetyl compounds, and others conventional in the art. Pyrazolone compounds are particularly useful. Specific examples of the magenta forming couplers used in the present invention are described in, e.g., U.S. Pat. Nos. 2,600,788, 2,983,608, 3,062,653, 3,127,269, 3,311,476, 3,419,391, 3,519,429, 3,558,319, 3,582,322, 3,615,605, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/75, Japanese Patent Application (OPI) Nos. 20826/76, 58922/77, 129538/74, 74027/74, 159336/75, 42121/77, 74028/74, 60233/75, 26541/76 and 55122/78.

Magenta couplers which can preferably be used in the present invention will be described below.

Most of the magenta couplers which have hitherto been studied and practically employed are 5-pyrazolone couplers. It is known that dye image forming from the 5-pyrazolone couplers are excellent in fastness to heat and light but show unnecessary absorption at about 430 nm due to a yellow component, which causes color turbidity.

Magenta image-forming coupler skeletons which have conventionally been proposed to lessen the yellow component include a pyrazolobenzimidazole skeleton as described in, e.g., British Pat. No. 1,047,612, an indazolone skeleton as described in, e.g., U.S. Pat. No. 3,770,447, and a pyrazolotriazole skeleton as described in, e.g., U.S. Pat. No. 3,725,067.

However, these conventionally proposed magenta couplers are still unsatisfactory, since, when mixed in the form of a dispersion in a hydrophilic colloid, such as gelatin, with a silver halide emulsion, they fail to produce satisfactory dye images, have poor solubility in high-boiling organic solvent, are difficult to synthesize, or exhibit only relatively low coupling activity with an ordinary developing solution.

The present inventors have now developed pyrazoloazole type magenta couplers, such a imidazo(1,2-b)pyrazoles, pyrazolo(1,5-b)(1,2,4)-triazoles, pyrazolo(1,5-d)tetrazoles, pyrazolo(1,5-d)benzimidazoles and pyrazolopyrazoles, which are free from the above-described disadvantages.

The above-described magenta couplers which can preferably be used in the present invention are represented by formula (XIV):

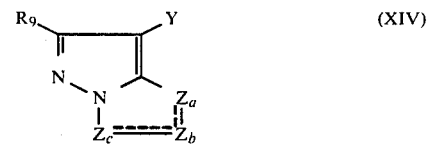

wherein $R_9$ represents a hydrogen atom, a halogen atom, a substituted or unsubstituted alkyl group, a substituted or unsubstituted aryl group, a substituted or unsubstituted heterocyclic group, a cyano group, a substituted or unsubstituted alkoxy group, a substituted or unsubstituted aryloxy group, a substituted or unsubstituted heterocyclic oxy group, a substituted or unsubstituted acyloxy group, a substituted or unsubstituted carbamoyloxy group, a substituted or unsubstituted silyloxy group, a substituted or unsubstituted sulfonyloxy group, a substituted or unsubstituted acylamino group, a substituted or unsubstituted anilino group, a substituted or unsubstituted ureido group, a substituted or unsubstituted imido group, a substituted or unsubstituted sulfamoylamino group, a substituted or unsubstituted carbamoylamino group, a substituted or unsubstituted alkylthio group, a substituted or unsubstituted arylthio group, a substituted or unsubstituted heterocyclic thio group, a substituted or unsubstituted alkoxycarbonylamino group, a substituted or unsubstituted aryloxycarbonylamino group, a substituted or unsubstituted sulfonamido group, a substituted or unsubstituted carbamoyl group, a substituted or unsubstituted acyl group, a substituted or unsubstituted sulfamoyl group, a substituted or unsubstituted sulfonyl group, a substituted or unsubstituted sulfinyl group, a substituted or unsubstituted alkoxycarbonyl group, or a substituted or unsubstituted aryloxycarbonyl group; Y represents a hydrogen atom or a group releasable upon coupling with an oxidation product of an aromatic primary amine developing agent; $Z_a$, $Z_b$ and $Z_c$ each represents a methine, a substituted methine, $=N-$ or $-NH-$; and either the $Z_a-Z_b$ bond or the $Z_b-Z_c$ bond is a double bond with the another being a single bond.

In the above-described formula (XIV), when $Z_b-Z_c$ represents a carbon-carbon double bond, it may form a condensed aromatic ring. The compounds of the formula (XIV) may include a polymer (e.g., a dimer, a trimer, etc.) formed at $R_9$ or Y. When $Z_a$, $Z_b$ or $Z_c$ is a substituted methine group, the compounds of the formula (XIV) may further include a polymer (e.g., a dimer, a trimer, etc.) formed at the substituted methine group.

The term "polymer" as used for the formula (XIV) means a polymeric compound comprising two or more repeating units represented by the formula (XIV), and includes a bis-compound and a polymer coupler. The polymer coupler as herein referred to may be either a homopolymer consisting solely of monomer units containing a vinyl group of formula (XIV) (hereinafter referred to as vinyl monomer), or a copolymer containing monomer (XIV) and a non-color forming ethylenic comonomer which is incapable of coupling with an oxidation product of an aromatic primary amine developing agent.

The compounds represented by the formula (XIV) are 5-membered-5-membered condensed nitrogen-containing heterocyclic couplers, having the color forming nuclei with aromaticity isoelectronic to naphthalene, and a chemical structure generally called "azapentalene". The compounds represented by the formula (XIV) are described in U.S. Pat. Nos. 3,369,879 and 3,725,067, and Research Disclosure Nos. 24220 (June, 1984) and 24230 (June, 1984).

Preferred compounds represented by formula (XIV) include 1H-imidazo(1,2-b)pyrazoles, 1H-pyrazolo(5,1-c)(1,2,4)triazoles, 1H-pyrazolo(1,5-b)pyrazoles, 1H-pyrazolo(1,5-b)(1,2,4)triazoles, 1H-pyrazolo(1,5-d)tetrazoles and 1H-pyrazolo(1,5-a)benzimidazoles, that are represented by the following formulae (XIV-1), (XIV-2), (XIV-3), (XIV-4), (XIV-5) and (XIV-6), respectively. Of these, the compounds of the formulae (XIV-1) and (XIV-4) are particularly preferred.

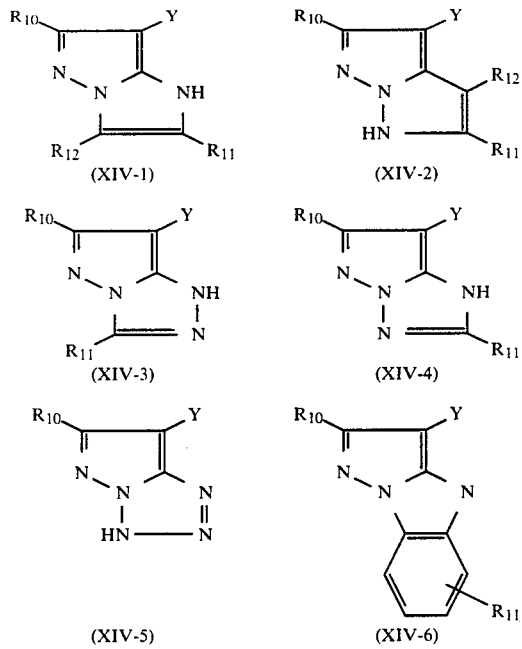

wherein $R_{10}$, $R_{11}$ and $R_{12}$ each represents a hydrogen atom, a halogen atom, a substituted or unsubstituted alkyl group, a substituted or unsubstituted aryl group, a substituted or unsubstituted heterocyclic group, a cyano group, a substituted or unsubstituted alkoxy group, a substituted or unsubstituted aryloxy group, a substituted or unsubstituted heterocyclic oxy group, a substituted or unsubstituted acyloxy group, a substituted or unsubstituted carbamoyloxy group, a substituted or unsubstituted silyloxy group, a substituted or unsubstituted sulfonyloxy group, a substituted or unsubstituted acylamino group, a substituted or unsubstituted anilino group, a substituted or unsubstituted ureido group, a substituted or unsubstituted imido group, a substituted or unsubstituted sulfamoylamino group, a substituted or unsubstituted carbamoylamino group, a substituted or unsubstituted alkylthio group, a substituted or unsubstituted arylthio group, a substituted or unsubstituted heterocyclic thio group, a substituted or unsubstituted alkoxycarbonylamino group, a substituted or unsubstituted aryloxycarbonylamino group, a substituted or unsubstituted sulfonamido group, a substituted or unsubstituted carbamoyl group, a substituted or unsubstituted acyl group, a substituted or unsubstituted sulfamoyl group, a substituted or unsubstituted sulfonyl group, a substituted or unsubstituted sulfinyl group, a substituted or unsubstituted alkoxycarbonyl group, or a substituted or unsubstituted aryloxycarbonyl group; and Y represents a hydrogen atom, a halogen atom, a carboxyl group, or a group which is bonded to the carbon atom at the coupling position via an oxygen atom, a nitrogen atom or a sulfur atom and which is releasable upon coupling reaction.

When $R_{10}$, $R_{11}$ and $R_{12}$ each has at least one substituent, $R_{10}$, $R_{11}$ and $R_{12}$ each represents a hydrogen atom, a halogen atom, an alkyl group, an aryl group a heterocyclic group, a cyano group, an alkoxy group, an aryloxy group, a heterocyclic oxy group, an acyloxy group, a carbamoyloxy group, a silyloxy group, a sulfonyloxy group, an acylamino group, a uredio group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamonyl group, an acyl group, a sulfamoyl group, a sulfonyl group, a sulfinyl group, an alkoxycarbonyl group, and an aryloxycarbonyl group.

When $R_{10}$, $R_{11}$, $R_{12}$ or Y represents a divalent group (hereinafter defined), the formulae (XIV-1) through (XIV-6) each includes the corresponding bis-compounds. Further, when the moiety represented by the formulae (XIV-1) to (XIV-6) is included in a vinyl monomer, $R_{10}$, $R_{11}$ or $R_{12}$ represents a mere bond or a linking group (hereinafter defined), by which the moiety of the formulae (XIV-1) to (XIV-6) is bonded to the vinyl group.

More specifically, $R_{10}$, $R_{11}$ and $R_{12}$ each represents a hydrogen atom, a halogen atom (e.g., a chlorine atom or a bromine atom), an alkyl group (e.g., a methyl group, a propyl group, a t-butyl group, a trifluoromethyl group, a tridecyl group, a 3-(2,4-di-t-amylphenoxy)propyl group, a 2-dodecyloxyethyl group, a 3-phenoxypropyl group, a 2-hexylsulfonylethyl group or a cyclopentyl group), a substituted or unsubstituted aralkyl group (e.g., a benzyl group), an aryl group (e.g., a phenyl group, a 4-t-butylphenyl group, a 2,4-di-t-amylphenyl group or a 4-tetradecaneamidophenyl group), a heterocyclic group (e.g., a 2-furyl group, a 2-thienyl group, a 2-pyrimidyl group or a 2-benzothiazolyl group), a cyano group, an alkoxy group (e.g., a methoxy group, an ethoxy group, a 2-methoxyethoxy group, a 2-dodecyloxyethoxy group or a 2-methanesulfonylethoxy group), an aryloxy group (e.g., a phenoxy group, a 2-methylphenoxy group or a 4-t-butylphenoxy group), a heterocyclic oxy group (e.g., a 2-benzimidazolyloxy group), an acyloxy group (e.g., an acetoxy group or a hexadecanoyloxy group), a carbamoyloxy group (e.g., an N-phenylcarbamoyloxy group or an N-ethylcarbamoyloxy group), a silyloxy group (e.g., a trimethylsilyloxy group), a sulfonyloxy group (e.g., a dodecylsulfonyloxy group), an acylamino group (e.g., an acetamido group, a benzamido group, a tetradecaneamido group, an α-(2,4-di-t-amylphenoxy)butylamido group, γ-(3-t-butyl-4-hydroxyphenoxy)butylamido group or an α-{4-(4-hydroxyphenylsulfonyl)phenoxy}decaneamido group), an anilino group (e.g., a phenylamino group, a 2-chloroanilino group, a 2-chloro-5-tetradecaneamidoanilino group, a 2-chloro-5-dodecyloxycarbonylanilino group, an N-acetylanilino group, a 2-chloro-5-{α-(3-t-butyl-4-hydroxyphenoxy)-dodecaneamido}anilino group), a ureido group (e.g., a phenylureido group, a methylureido group or an N,N-dibutylureido group), an imido group (e.g., an N-succinimido group, a 3-benzylhydantoinyl group or a 4-(2-ethylhexanoylamino)phthalimido group), a sulfamoylamino group (e.g., an N,N-dipropylsulfamoylamino group or an N-methyl-N-decylsulfamoylamino group), a carbamoylamino group, an alkylthio group (e.g., a methylthio group, an octylthio group, a tetradecylthio group, a 2-phenoxyethylthio group, a 3-phenoxypropylthio group or a 3-(4-t-butylphenoxy)propylthio group), an arylthio group (e.g., a phenylthio group, a 2-butoxy-5-t-octylphenylthio group, a 3-pentadecylphenylthio group, a 2-carboxyphenylthio group or a 4-tetradecaneamidophenylthio group), a heterocyclic thio group (e.g., a 2-benzothiazolylthio group), an alkoxycarbonylamino group (e.g., a methoxycarbonylamino group or a tetradecyloxycarbonylamino group), an aryloxycarbonylamino group (e.g., a phenoxycarbonylamino group or a 2,4-di-t-butylphenoxycarbonylamino group), a sulfonamido group (e.g., a methanesulfonamido group, a hexadecanesulfonamido group, a benzenesulfonamido group, a p-toluenesulfonamido group, an octadecanesulfonamido group or a 2-methyloxy-5-t-butylbenzenesulfonamido group), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group or an N-[3-(2,4-di-t-amylphenoxy)propyl]carbamoyl group), an acyl group (e.g., an acetyl group, a (2,4-di-t-amylphenoxy)acetyl group or a benzoyl group), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group or an N,N-diethylsulfamoyl group), a sulfonyl group (e.g., a methanesulfonyl group, an octanesulfonyl group, a benzenesulfonyl group or a toluenesulfonyl group), a sulfinyl group (e.g., an octanesulfinyl group, a dodecylsulfinyl group or a phenylsulfinyl group), an alkoxycarbonyl group (e.g., a methoxycarbonyl group, a butyloxycarbonyl group, a dodecyloxycarbonyl group or an octadecyloxycarbonyl group), or an aryloxycarbonyl group (e.g., a phenyloxycarbonyl group or a 3-pentadecyloxycarbonyl group); and Y represents a hydrogen atom, a halogen atom (e.g., a chlorine atom, a bromine atom or an iodine atom), a carboxyl group, a group bonded via an oxygen atom (e.g., an acetoxy group, a propanoyloxy group, a benzoyloxy group, a 2,4-dichlorobenzoyloxy group, an ethoxyoxaloyloxy group, a pyruvinyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group or a 2-benzothiazolyloxy group), a group bonded via a nitrogen atom (e.g., a benzenesulfonamido group, an N-ethyltoluenesulfonamido group, a heptafluorobutaneamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzylethoxy-3-hydantoinyl group, a 2N-1,1-dioxo-3(2H)-oxo-1,2-benzoisothiazolyl group, a 2-oxo-1,2-dihydro-1-pyridinyl group, an imidazolyl group, a pyrazolyl group, a 3,5-diethyl-1,2,4-triazol-1-yl group, a 5- or 6-bromo-benzotriazol-1-yl group, a 5-methyl-1,2,3,4-triazol-1-yl group, a benzimidazolyl group, a 3-benzyl-1-hydantoinyl group, a 1-benzyl-5-hexadecyloxy-3-hydantoinyl group, a 5-methyl-1-tetrazolyl group, a 4-methoxyphenylazo group, a 4-pivaloylaminophenylazo group or a 2-hydroxy-4-propanoylphenylazo group), or a group bonded via a sulfur atom (e.g., a phenylthio group, a 2-carboxyphenylthio group, a 2-methoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-t-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, a 2-dodecylthio-5-thiophenylthio group or a 2-phenyl-3-dodecyl-1,2,4-triazolyl-5-thio group).

When $R_{10}$, $R_{11}$, $R_{12}$ or Y is a divalent group forming a bis-compound, such a divalent group includes a substituted or unsubstituted alkylene group (e.g., a methylene group, an ethylene group, a 1,10-decylene group or —CH$_2$CH$_2$—O—CH$_2$CH$_2$—), a substituted or unsubstituted phenylene group (e.g., a 1,4-phenylene group, a 1,3-phenylene group,

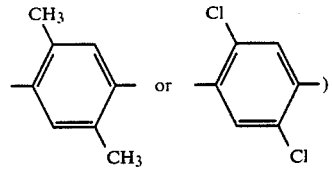

and a —NHCO—$R_{13}$—CONH— group, wherein $R_{13}$ represents a substituted or unsubstituted alkylene or phenylene group.

When the structure represented by formulae (XIV-1) to (XIV-6) is contained in the vinyl monomer, the linking group represented by $R_{10}$, $R_{11}$ or $R_{12}$ includes a substituted or unsubstituted alkylene group (e.g., a methylene group, an ethylene group, a 1,10-decylene group or —CH$_2$CH$_2$OCH$_2$CH$_2$—), a substituted or unsubstituted phenylene group (e.g., a 1,4-phenylene group, a 1,3-phenylene group,

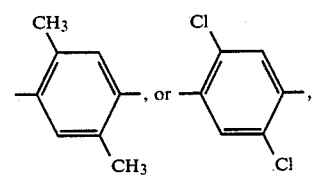

—NHCO—, —CONH—, —O—, —CO— and a substituted or unsubstituted aralkylene group (e.g.,

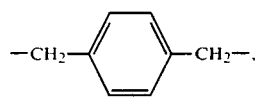

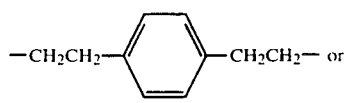

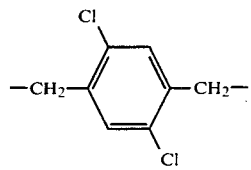

and a combination thereof.

The vinyl group in the vinyl monomer includes, in addition to those represented by the formulae (XIV-1) through (XIV-6), those having a substituent. Such a substituent preferably includes a hydrogen atom, a chlorine atom and a lower alkyl group having from 1 to 4 carbon atoms.

The non-color forming ethylenic comonomer incapable of coupling with an oxidation product of an aromatic primary amine developing agent can include acrylic acid, α-chloroacrylic acid, an α-alkylacrylic acid (e.g., methacrylic acid), esters or amides derived from these acrylic acids (e.g., acrylamide, n-butylacrylamide, t-butylacrylamide, diacetoneacrylamide, methacrylamide, methyl acrylate, ethyl acrylate, n-propyl acrylate, n-butyl acrylate, t-butyl acrylate, iso butyl acrylate, 2-ethylhexyl acrylate, n-octyl acrylate, lauryl acrylate, methyl methacrylate, ethyl methacrylate, n-butylmethacrylate and β-hydroxy methacrylate), methlenedibisacrylamide, a vinyl ester (e.g., vinyl acetate, vinyl propionate and vinyl laurate), acrylonitrile, methacrylonitrile, an aromatic vinyl compound (e.g., styrene and derivatives thereof, vinyltoluene, divinylbenzene, vinylacetophenone and sulfostyrene), itaconic acid, citraconic acid, crotonic acid, vinylidene chloride, a vinyl alkyl ether (e.g., vinyl ethyl ether), maleic acid, maleic anhydride, a maleic ester, N-vinyl-2-pyrrolidone, N-vinylpyridine, 2- or 4-vinylpyridine, and the like. These non-color forming ethylenically unsaturated monomers can be used individually or in combinations of two or more thereof.

Specific examples of the compounds of formula (XIV-1) and the process for synthesizing them are described in European Pat. No. 119,741. Specific examples of the compounds of the formula (XIV-2) and the process for synthesizing them are described in, e.g., Research Disclosure, No. 24230 (June, 1984). Specific examples of the compounds of the formula (XIV-3) and the process for synthesizing them are described in, e.g., Japanese Patent Publication No. 27411/72 corresponding to British Pat. No. 1,247,493. Specific examples of the compounds of the formula (XIV-4) and the process for synthesizing them are described in, e.g., European Pat. No. 119,860. Specific examples of the compounds of the formula (XIV-5) and the process for synthesizing them are described in, e.g., Research Disclosure, No. 24220 (June, 1984). Specific examples of the compounds of the formula (XIV-6) and the process for synthesizing them are described in, e.g., U.S. Pat. Nos. 3,061,432 and 3,369,879.

Further, the ballast groups having high color forming activity as disclosed in Japanese Patent Application (OPI) No. 42045/83 can be contained in any of the compounds of the formulae (XIV-1) through (XIV-6).

Specific examples of the pyrazoloazole type couplers which can be used in the present invention are shown below, but the present invention is not limited thereto.

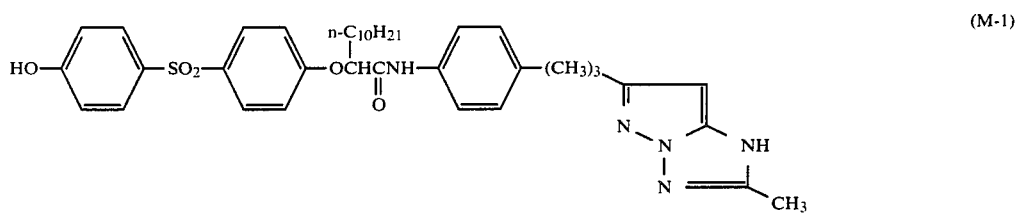

(M-1)

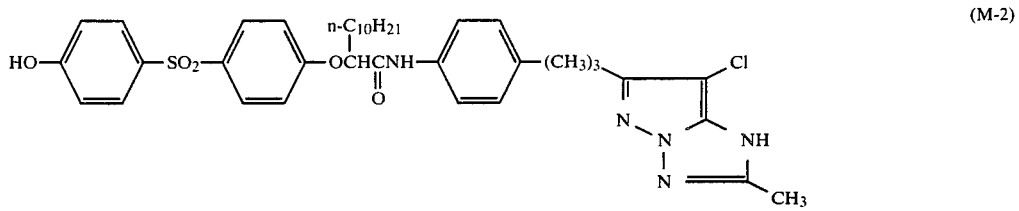

(M-2)

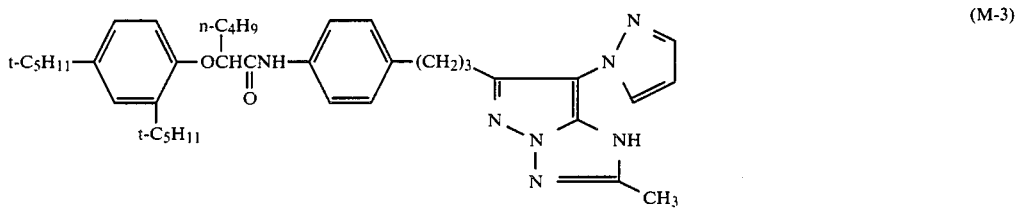

(M-3)

-continued
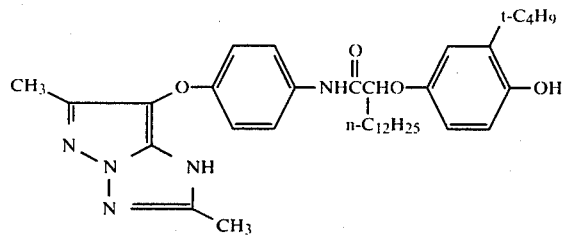 (M-4)
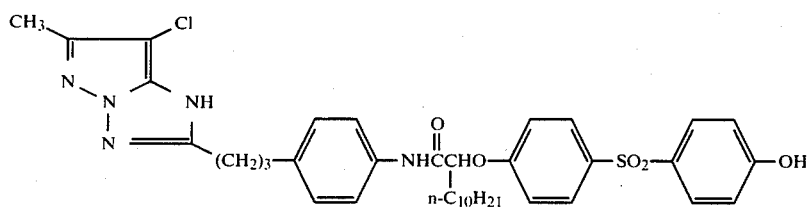 (M-5)
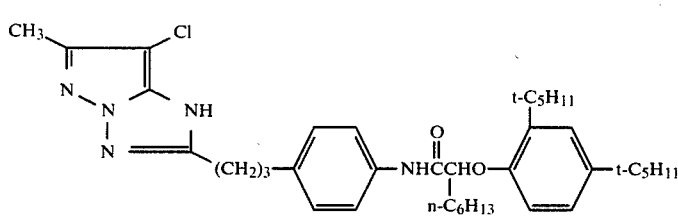 (M-6)
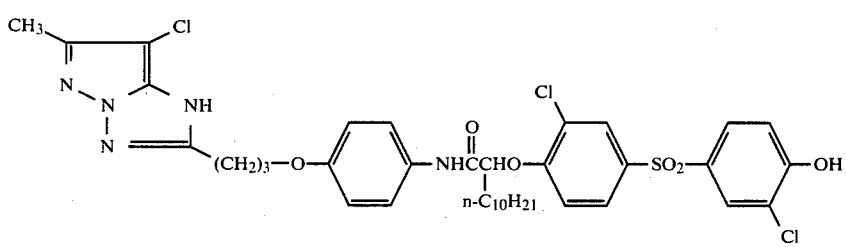 (M-7)
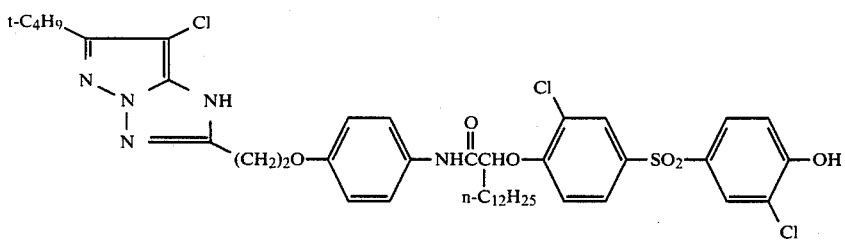 (M-8)
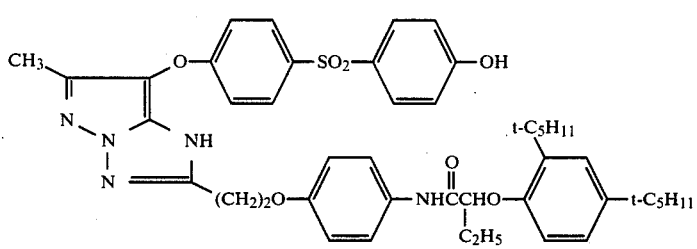 (M-9)
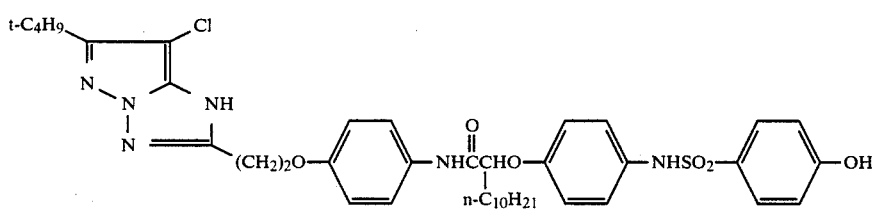 (M-10)

-continued
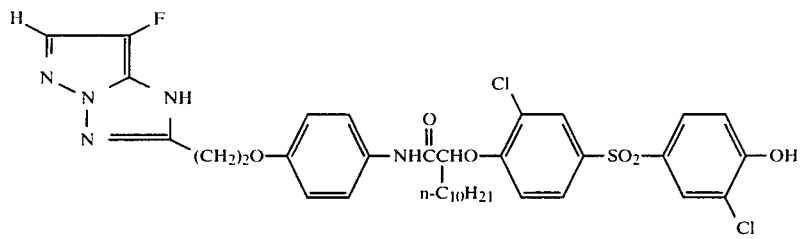
(M-11)
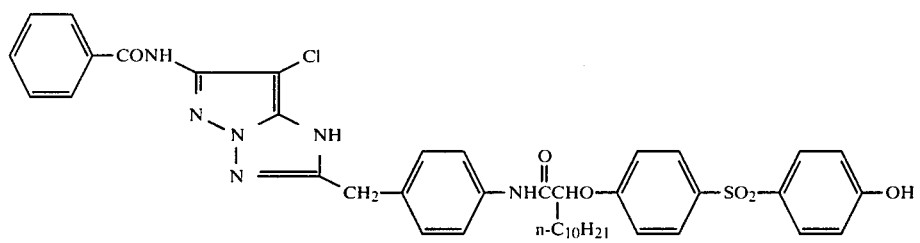
(M-12)
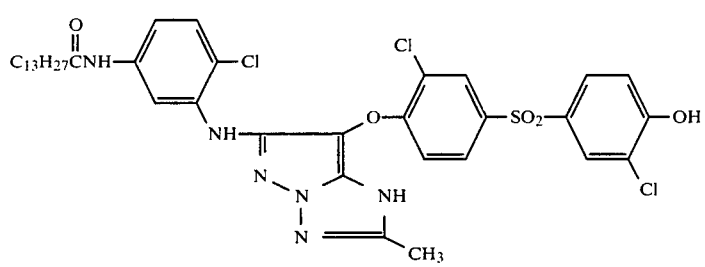
(M-13)
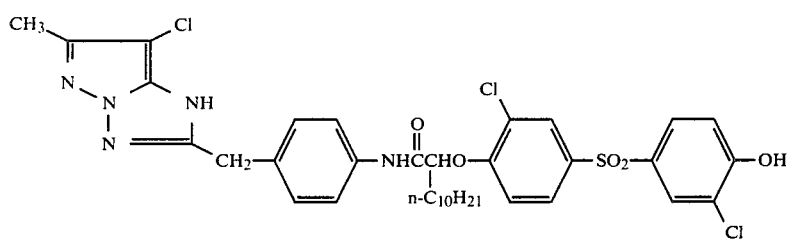
(M-14)
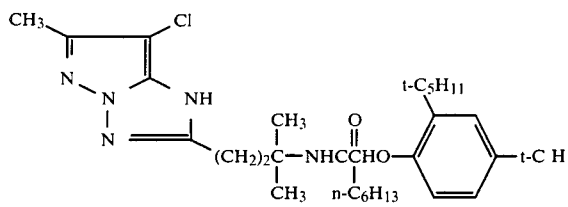
(M-15)
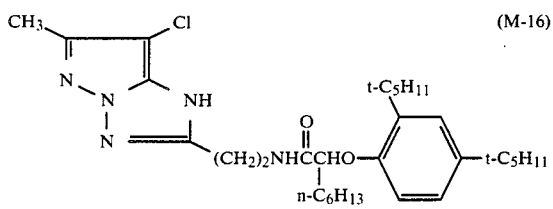
(M-16)
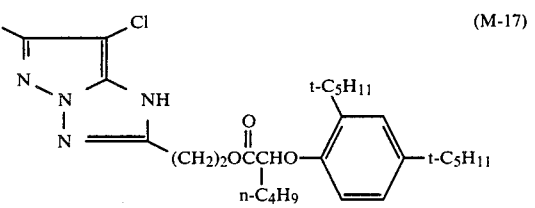
(M-17)

-continued
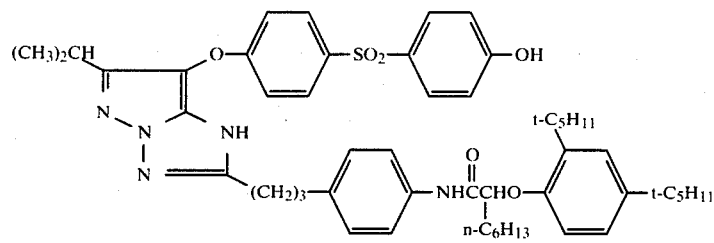
(M-18)
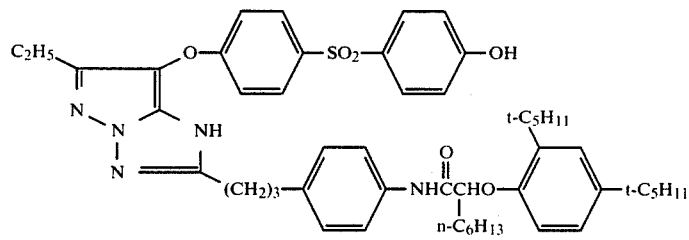
(M-19)
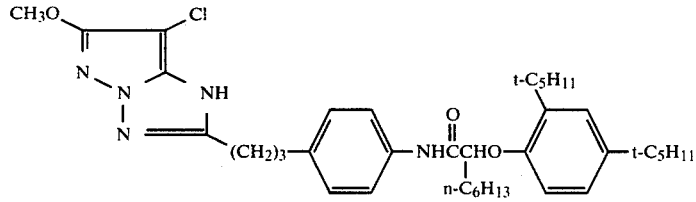
(M-20)
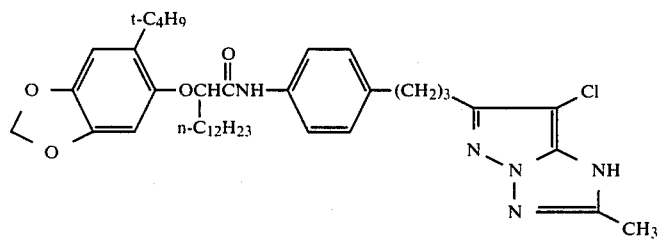
(M-21)
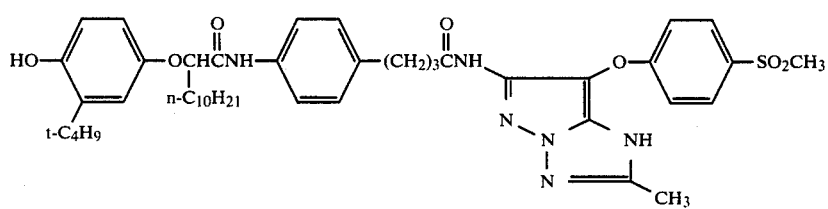
(M-22)
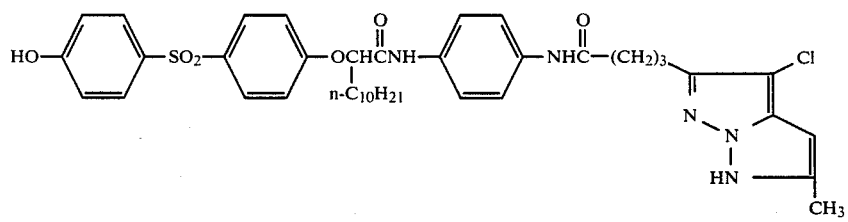
(M-23)
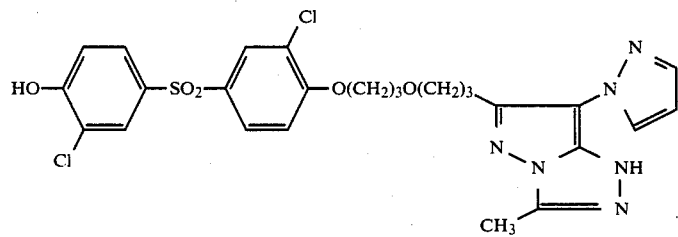
(M-24)

-continued
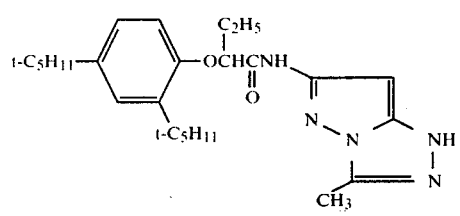 (M-25)
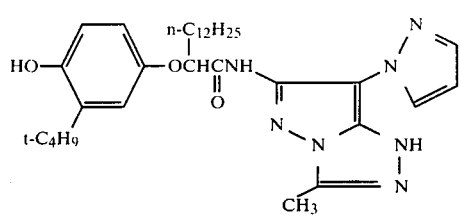 (M-26)
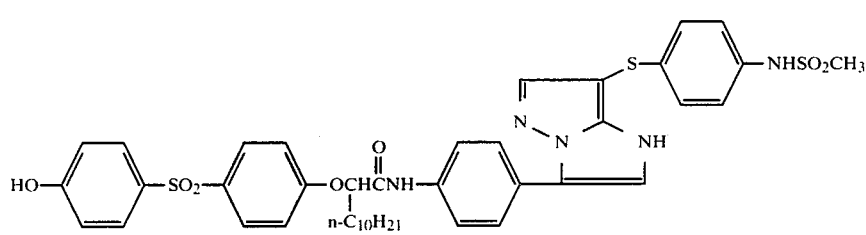 (M-27)
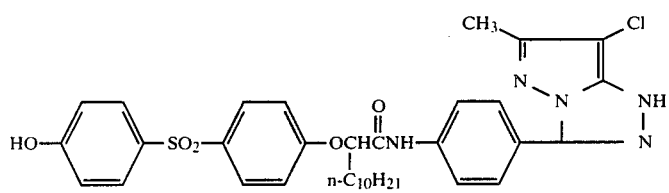 (M-28)
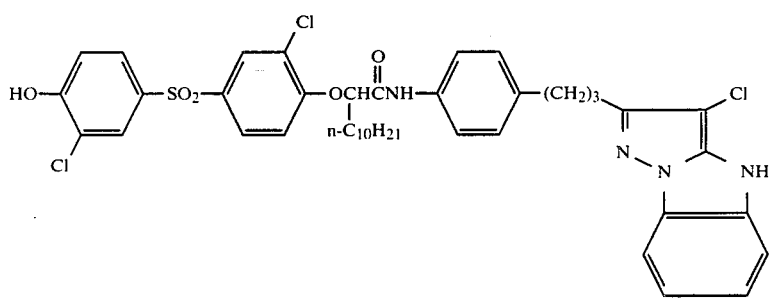 (M-29)
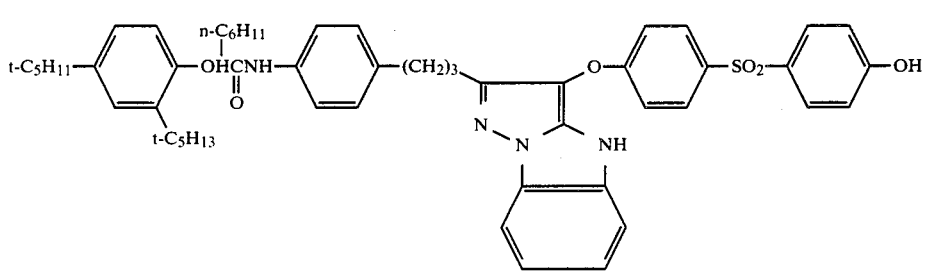 (M-30)
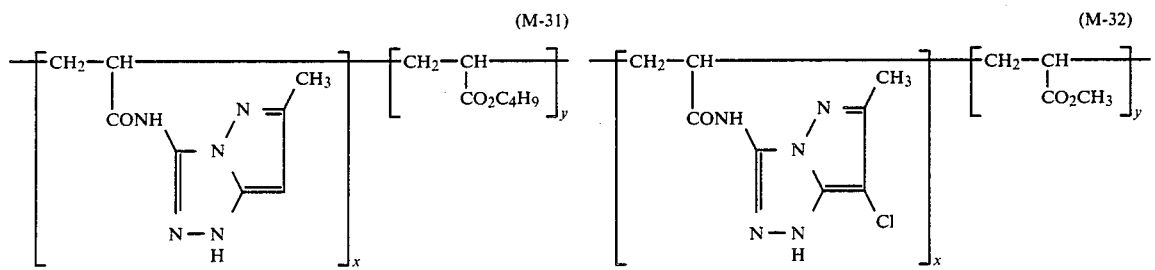
(M-31) x:y = 50:50
(M-32) x:y = 40:60

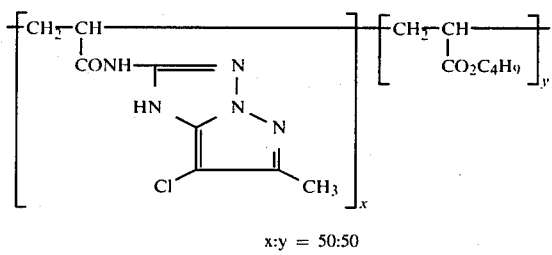

(M-33)

x:y = 50:50

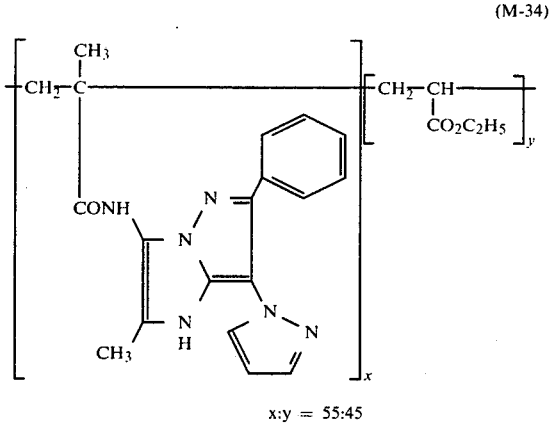

(M-34)

x:y = 55:45

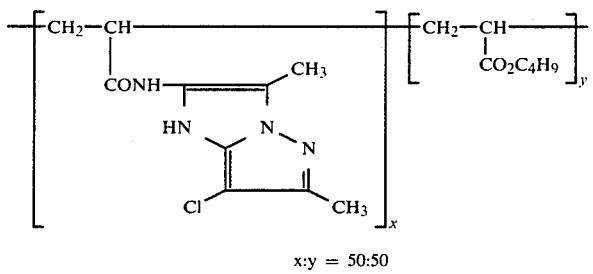

(M-35)

x:y = 50:50

The above-described coupler according to the present invention is added to a photographic emulsion layer in an amount of from about $2 \times 10^{-3}$ to $5 \times 10^{-1}$ mol, and preferably from about $1 \times 10^{-2}$ to $5 \times 10^{-1}$ mol, per mol of silver contained in the emulsion layer.

In the present invention, it is preferred that the pyrazoloazole type coupler represented by the formula (XIV) is incorporated in the same emulsion layer in which the stabilizer represented by the formula (I) is incorporated.

Cyan couplers which can be used in the present invention include phenol couplers, naphthol couplers, and other cyan couplers conventional in the art. Specific examples of usable cyan couplers are given in, e.g., U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 69624/77 and 90932/77.

Colored couplers which can be used in the present invention include those described in, e.g., U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and West German Patent Application (OLS) No. 2,418,959.

DIR couplers which can be used in the present invention include those described in, e.g., U.S. Pat. Nos. 227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application (OPI) Nos. 69624/77 and 122335/74, and Japanese Patent Publication No. 16141/76.

In addition to the DIR couplers, the light-sensitive material according to the present invention may contain a compound capable of releasing a development inhibitor with the progress of development, such as those described in, e.g., U.S. Pat. Nos. 3,297,445 and 3,379,529, West German Patent Application (OLS) No. 2,417,914, Japanese Patent Application (OPI) Nos. 15271/77 and 9116/78.

The above-described couplers can be contained in one layer in combinations of two or more of them, or the same compound can be present in two or more different layers.

Incorporation of the compound represented by the formula (I) according to the present invention in a photographic layer of the light-sensitive material may be carried out by dissolving it in a low-boiling organic solvent, such as ethyl acetate or ethanol, or adding it directly to a coating composition for a photographic layer or a mixed solution of a coupler dispersion without being emulsified. However, it is desirable that the compound of the formula (I) is incorporated into a photographic layer by dissolving in a high-boiling solvent, such as dibutyl phthalate or tricresyl phosphate, if necessary, with the aid of a low-boiling auxiliary solvent, dispersing the solution in a water-soluble protective colloid, such as gelatin, and adding the resulting oil-in-water emulsified dispersion to a coating composition for a photographic layer. If using a coupler in the latter case, the coupler may be added to the emulsified dispersion, or a coupler dispersion may be separately prepared and then mixed with the emulsified dispersion and added to a coating composition for a photographic layer.

Typical examples of high-boiling organic solvents which can be used for dispersing the compound of formula (I) include those described in U.S. Pat. No. 3,676,137, such as phthalic esters, including butyl phthalate, butyl benzoate, diethylhexyl sebacate, butyl stearate, dinonyl maleate, tributyl citrate and tri-cresyl phosphate; diethyl succinate, dioctyl adipate, 3-ethylbiphenol; and the liquid dye stabilizers disclosed in Product Licensing Index, 83, 26–29 (March, 1971) as "Improved Photographic Dye Image Stabilizers".

Examples of the low-boiling organic solvents which can be used as an auxiliary solvent for the high-boiling organic solvent include lower fatty acid esters, e.g., ethyl acetate, hydrocarbons, e.g., hexane and toluene, ethylene glycol, acetone, ethanol, dimethylformamide, dioxane, and other conventional solvent with a boiling point lower than about 175° C.

Surface active agents which can be used for dispersing a solution of the compounds of formula (I) in an aqueous protective colloidal solution include saponin, sodium alkylsulfosuccinates and sodium alkylbenzenesulfonates. The hydrophilic protective colloids which can be used in the present invention can include gelatins (e.g., lime-processed gelatin and acid-processed gelatin), casein, carboxymethyl cellulose, polyvinyl alcohol, polyvinylpyrrolidone, a styrene-maleic anhydride copolymer, a condensate of a styrene-maleic anhydride copolymer and polyvinyl alcohol, a polyacrylic acid salt and ethyl cellulose. However, it should be understood that the above-recited specific examples are not to be construed as limiting the present invention.

A silver halide emulsion which can be used in the present invention is generally prepared by mixing a solution of a water-soluble silver salt (e.g., silver nitrate) and a solution of a water-soluble halogen salt (e.g., potassium bromide) in the presence of a solution of a water-soluble high polymer, such as gelatin. The silver halide may be any of silver chlorobromide, silver iodobromide, silver chloroiodobromide.

The mean grain size of silver halide grains in the silver halide emulsion (the grain size being defined as grain diameter if the grain has a spherical or a nearly spherical form and as a length of the edge if the grain has a cubic form, and being averaged based on projected areas of the grains) is preferably about 2 $\mu$m or less, and more preferably about 0.4 $\mu$m or less. Grain size distribution may be either narrow or broad.

The silver halide grains in the photographic emulsion may have a regular crystal form, such as cubic and octahedral, an irregular crystal form, such as spherical and plate-form, or a composite form thereof. An emulsion wherein plate-form silver halide grains having a diameter/thickness ratio of about 5 or more, and preferably about 8 or more, occupy not less than 50% of the total projection area of the total grains can also be employed.

Two or more silver halide photographic emulsions prepared separately may be used as a mixture.

The silver halide grains may have a homogeneous crystal structure, a layered structure comprising a core and an outer shell, or a so-called conversion form as described in British Pat. No. 635,841 and U.S. Pat. No. 3,662,318. Further, the grains may be either a surface latent image type or an inner latent image type. These photographic emulsions are described in, e.g., Mees, *The Theory of Photographic Process* (MacMillan), P. Glafkides, *ChimiePhotographique* (Paul Montel, 1957), and are widely known. The above-described photographic emulsions can be prepared according to conventional methods, as described in, e.g., P. Glafkides, *Chimie et Physique Photographique* (Paul Montel, 1967), G. F. Duffin, *Photographic Emulsion Chemistry* (The Focal Press, 1966), and V. L. Zelikman et al., *Making and Coating Photographic Emulsion* (The Focal Press, 1964). That is, photographic emulsions can be prepared according to any of the acid process, the neutral process, the ammonia process, and the like. Methods of reacting a water-soluble silver salt with a water-soluble halogen salt include the single jet method, the double jet method, and a combination thereof.

In addition, a method in which silver halide grains are produced in the presence of excess silver ions (the so-called reverse mixing method) can also be employed. Further, the so-called controlled double jet method, in which the pAg of the liquid phase wherein silver halide grains are to be precipitated is maintained constant, can be used. According to this method, silver halide emulsions in which grains have a regular crystal form and an almost uniform size distribution can be obtained.

In a process of producing silver halide grains or physically ripening the produced silver halide grains, cadmium salts, zinc salts, lead salts, thallium salts, iridium salts or complexes thereof, rhodium salts or complexes thereof, or iron salts or complexes thereof may be used.

The so-called primitive silver halide emulsions which have not been subjected to chemical sensitization may be employed, but it is usual for the emulsion to be chemically sensitized. Chemical sensitization can be carried out in accordance with the methods described in, e.g., the above-mentioned references written by Glafkides or Zelikman et al., or H. Frieser (ed.), *Die Grundlagen der Photographischen Prozesse mit Silberhalogeniden*, (Akademische Verlagsgesellschaft, 1968).

The photographic emulsions which can be used in the present invention may be spectrally sensitized with methine dyes and others. Sensitizing dyes to be used include cyanine dyes, merocyanine dyes, complex cyanine dyes, complex merocyanine dyes, holopolar cyanine dyes, hemicyanine dyes, styryl dyes and hemioxonol dye, with cyanine dyes, mercyanine dyes and complex mercocyanine dyes being particularly useful.

These sensitizing dyes may be used individually or in combinations thereof. Combinations of sensitizing dyes are frequently employed for the purpose of supersensitization.

In carrying out the present invention, known discoloration preventing agents can be used in combination with the stabilizers of the formula (I) according to the present invention. Further, the color image stabilizers according to the present invention can be used alone or in combination of two or more thereof. Examples of known discoloration preventing agents include hydroquinone derivatives as described in, e.g., U.S. Pat. Nos. 2,360,290, 2,418,613, 2,675,314, 2,701,197, 2,704,713, 2,728,659, 2,732,300, 2,735,765, 2,710,801 and 2,816,028, and British Pat. No. 1,363,921; gallic acid derivatives as described in, e.g., U.S. Pat. Nos. 3,457,079 and 3,069,262; p-alkoxyphenols as described in, e.g., U.S. Pat. Nos. 2,735,765 and 3,698,909, Japanese Patent Publication Nos. 20997.74 and 6623/77; p-oxyphenol derivatives as described in, e.g., U.S. Pat. Nos. 3,432,300, 3,573,050, 3,574,627 and 3,764,337, Japanese Patent Application (OPI) Nos. 35633/77, 14743/77 and 152225/77; and bisphenols as described in, e.g., U.S. Pat. No. 3,700,455.

Supports which can be used in the present invention generally include films made of cellulose acetate, cellulose acetate butyrate, polyethylene terephthalate, or polycarbonate, laminates of these polymers, glass, paper, and the like. Paper supports coated or laminated with a baryta layer or an $\alpha$-olefin polymer (particularly, a polymer of an $\alpha$-olefin having from 2 to 10 carbon atoms, e.g., polyethylene, polypropylene, or an ethylene-butene copolymer) and plastic films having a roughened surface to improve adhesiveness to other high polymeric substances, disclosed in Japanese Patent Publication No. 19068/72, can also be used to advantage.

A transparent or opaque support can be selected from these supports depending on the particular use of the light-sensitive material. Further, the supports may be colored with dyes or pigments.

Opaque supports include originally opaque paper, films rendered opaque by dyes or pigments, e.g., titanium oxide, plastic films subjected to surface treatment disclosed in Japanese Patent Publication No. 19068/72, and paper or plastic films having been rendered completely light-shielding by adding carbon black or dyes. On the surfaces of these supports a subbing layer is generally provided to increase adhesiveness to photographic emulsion layers. In order to further improve adhesiveness of the supports, the surface of the supports may be preliminarily treated by corona discharge, ultraviolet irradiation, flame treatment, and the like.

In carrying out the present invention, it is preferable to provide an ultraviolet aborbing layer on the photographic light-sensitive emulsion layer to ensure prevention of discoloration or decoloration due to light, as is described in Research Disclosure, No. 24239 (June, 1984), etc.

Any conventional photographic processing, whether for the formation of silver images or for the formation of dye images, can be applied to the light-sensitive material of the present invention according to the end use thereof.

Furthermore, the present invention is not limited by the type of color processing agents, such as color developing agents, bleaching agents, fixing agents, and the like. In particular, the present invention can advantageously be applied to the silver-saving type color light-sensitive materials as disclosed in U.S. Pat. No. 3,902,905. Furthermore, the present invention is not limited by the type of intensifiers for color intensification, as described in, e.g., West German Patent Application (OLS) No. 1,813,920, Japanese Patent Application (OPI) No. 9728/73, or Japanese Patent Publication No. 14625/77.

According to the present invention, the color photographic light-sensitive material should be subjected to color photographic development processing after exposure to light in order to obtain a dye image. Color photographic development processing basically involves color development, bleaching and fixing steps. Two steps may be combined into one processing step in some cases. Moreover, a combination of color development, first fixing and bleaching-fixing may also be employed. The development processing step typically comprises pre-hardening, neutralization, first development (achromatic development), image stabilization, and washing with water according to necessity. The processing temperature generally employed is about 18° C. or higher, and more generally from about 20° to 60° C. In particular, a temperature range of from about 30° to 60° C. has recently been used.

A color developing solution generally comprises an aqueous alkaline solution having a pH of about 8 or more, and preferably from about 9 to 12, containing an aromatic primary amine color developing agent. Typical examples of the color developing agents which can preferably be used include 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and salts thereof (e.g., a sulfate, hydrochloride, a sulfite, or a p-toluenesulfonate). In addition, examples of usable color developing agents are given in U.S. Pat. Nos. 2,193,015 and 2,592,364, Japanese Patent Application (OPI) No. 64933/73, and L. F. A. Mason, *Photographic Processing Chemistry*, 226–229 (Focal Press, London), (1966).

The color developing solution can further contain a pH buffer, e.g., a sulfite, carbonate, borate or phosphate of an alkali metal, a development inhibitor or antifoggant, e.g., a bromide, an iodide and an organic antifoggant, a fluorescent brightening agent, and other conventional additives.

The color developing solution can additionally contain, if desired, water softener, a preservative, e.g., hydroxylamine, an organic solvent, e.g., benzyl alcohol, diethylene glycol, a development accelerator, e.g., polyethylene glycol, a quaternary ammonium salt and an amine, a color forming coupler, a competing coupler, a fogging agent, e.g., sodium borohydride, an auxiliary developing agent, e.g., 1-phenyl-3-pyrazolidone, and a viscosity-imparting agent.

The color light-sensitive material containing the compound represented by the formula (I) according to the present invention is subjected to ordinary color development processing. Color intensification processing can also be applied to the light-sensitive material. Such color intensification can be carried out by conventional methods, such as the method using peroxides, disclosed in U.S. Pat. Nos. 3,674,490 and 3,761,265, West German Patent Application (OLS) No. 2,056,360, Japanese Patent Application (OPI) Nos. 6338/72, 10538/72, 13334/77, 13335/77 and 13336/77; the method using cobalt complex salts, as disclosed in West German Patent Application (OLS) No. 2,226,770, Japanese Patent Application (OPI) Nos. 9728/73, 9729/73, 6026/76, 94822/76, 133023/76, 7728/77 and 11034/77; and the method using chlorous acid, as disclosed in Japanese Patent Publication No. 14625/77, Japanese Patent Application (OPI) Nos. 99022/76 and 103430/76.

After color development, the photographic emulsion is generally subjected to bleaching treatment. Bleaching may be carried out simultaneously with fixing, or these two processes may be carried out separately. Examples of bleaching agents which can be used include compounds of polyvalent metals, e.g., iron (III), cobalt (III), chromium (VI), and copper (II), peroxy acids, quinones, and nitroso compounds. Specific examples of the bleaching agents include ferricyanides; bichromates; organic complex salts formed by iron (III) or cobalt (III) and aminopolycarboxylic acids, e.g., ethylenediaminetetraacetic acid, nitrilotriacetic acid and 1,3-diamino-2-propanoltetraacetic acid, or organic acids, such as citric acid, tartaric acid or malic acid; persulfates and permanganates; and nitrosophenol. Among these agents, potassium ferricyanide, sodium (ethylenediaminetetraacetato)ferrate (III) and ammonium (ethylenediaminetetraacetato)ferrate (III) are particularly useful. The (ethylenediaminetetraacetato)ferrate (III) complexes are useful in both an independent bleaching solution and a combined bleach-fix bath.

The bleaching or the bleach-fix bath can contain various additives, such as a bleach accelerating agents, as described in, e.g., U.S. Pat. Nos. 3,042,520 and 3,241,966, Japanese Patent Publication Nos. 8506/70 and 8836/70.

The present invention will now be illustrated in greater detail with reference to the following examples, but it should be understood that these examples are not to be construed as limiting the present invention. In these examples, all percents, ratios and parts are by weight unless otherwise indicated.

EXAMPLE 1

In a mixed solvent of 20 ml of tricresyl phosphate and 20 ml of ethyl acetate was dissolved 10 g of 1-(2,4,6-trichlorophenyl)-3-[(2-chloro-5-tetradecaneamido)anilino-]-2-pyrazolin-5-one as a magenta coupler (hereinafter designated as Coupler (a)). The solution was emulsified and dispersed in 80 g of a 10% gelatin solution containing 8 ml of a 1% aqueous solution of sodium dodecylbenzenesulfonate. The resulting emulsified dispersion was mixed with 145 g of a green-sensitive silver chlorobromide emulsion (Br content: 50 mol%; Ag content: 7 g), and 1.5 ml of 5% aqueous solution of sodium dodecylbenzenesulfonate was added thereto as a coating aid. The resulting coating composition was applied onto a paper support laminated with a polyethylene layer on both sides thereof to a coupler coverage of 400 mg/m². A gelatin protective layer containing 1 g/m² of gelatin was formed on the silver halide emulsion layer. The resulting sample was designated as Sample A-1.

Samples A-2 to A-10 were produced in the same manner as described above except that a dye image stabilizer as shown in Table 1 was added to the emulsified dispersion in an amount of 50 mol% based on coupler (a).

Each of the resulting samples was exposed to light at 1,000 lux for 1 second and subjected to development processing as shown below with a processing solution having the following compositions.

| Processing Step: | Temperature | Period |
|---|---|---|
| Development | 33° C. | 3' 30" |
| Bleach-Fixing | 33° C. | 1' 30" |
| Washing with Water | 28–35° C. | 3' |

| Developing Solution: | |
|---|---|
| Benzyl alcohol | 15 ml |
| Diethylenetriaminepentaacetic acid | 5 g |
| Potassium bromide | 0.4 g |
| Sodium sulfite | 5 g |
| Sodium carbonate | 30 g |
| Hydroxylamine sulfate | 2 g |
| 4-Amino-3-methyl-N—ethyl-N—β-(methanesulfonamido)ethylaniline 3/2 H₂SO₄·H₂O | 4.5 g |
| Water to make | 1000 ml |
| | (pH = 10.1) |

| Bleach-Fixing Solution: | |
|---|---|
| Ammonium thiosulfate (70%) | 150 ml |
| Sodium sulfite | 5 g |
| Sodium (ethylenediaminetetra-acetato)ferrate | 40 g |
| Ethylenediaminetetraacetic acid | 4 g |
| Water to make | 1000 ml |
| | (pH = 6.8) |

Each of the thus processed samples having formed thereon a dye image was tested for light-fastness, that is, the samples were exposed with a filter preventing light of 400 nm or less from reaching the samples with an ultraviolet-absorbing filter that intercepted in a fade meter using a xenon lamp (200,000 lux) for 5 days. Changes in density of the image area having an initial density of 2.0 and the white background of the non-image area were determined by the use of a Macbeth densitometer, RD-514 (Status AA Filter). The results obtained are shown in Table 1.

TABLE 1

| | | Change in Density | | |
|---|---|---|---|---|
| Sample No. | Dye Image Stabilizer | White Background | Initial Density = 2.0 | Remark |
| A-1 | — | +0.28 | −1.54 | Comparison |
| A-2 | Compound No. 1 | +0.11 | −0.48 | Invention |
| A-3 | Compound No. 3 | +0.12 | −0.37 | " |
| A-4 | Compound No. 4 | +0.09 | −0.36 | " |
| A-5 | Compound No. 12 | +0.12 | −0.29 | " |
| A-6 | Compound No. 14 | +0.08 | −0.35 | " |
| A-7 | Compound No. 17 | +0.13 | −0.49 | " |
| A-8 | Comparative Compound (a) | +0.23 | −0.98 | Comparison |
| A-9 | Comparative Compound (b) | +0.22 | −0.62 | " |
| A-10 | Comparative Compound (c) | +0.24 | −0.56 | " |

Comparative Compound (a):

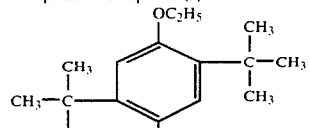

Comparative Compound (b):

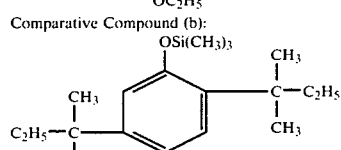

Comparative Compound (c):

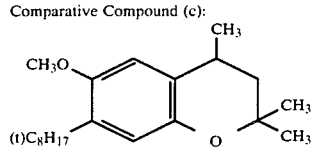

From the results shown in Table 1, it can be seen that the compounds of formula (I) according to the present invention are effective to prevent dye images from decoloration due to exposure to light and also to prevent white background from yellowing due to exposure to light.

EXAMPLE 2

Sample B-1 was produced in the same manner as described for Sample A-1 in Example 1.

Samples B-2 to B-6 were produced in the same manner as for Sample B-1 except that the dye image stabilizer indicated in Table 2 was added to the emulsified dispersion in an amount of 50 mol% based on the coupler used.

Samples B-7 to B-20 were produced in the same manner as for Sample B-1 except that Magenta Coupler (a) was replaced by a magenta coupler of the formula (XIV) indicated in Table 2 and the dye image stabilizer as indicated in Table 2 was added to the emulsified dispersion in an amount of 50 mol% based on the coupler used.

Each of the resulting samples was exposed to light and processed in the same manner as described in Example 1.

Each of the processed samples having formed thereon a dye image was subjected to a decoloration test in the same manner as in Example 1 to determine changes in density of the area having an initial density of 2.0. The results obtained are shown in Table 2.

TABLE 2

| Sample No. | Magenta Coupler | Dye Image Stabilizer | Change of Density | Remark |
|---|---|---|---|---|
| B-1 | (a) | — | −1.70 | Comparison |
| B-2 | " | Comparative Compound (d) | −0.54 | " |
| B-3 | " | Comparative Compound (e) | −0.49 | " |
| B-4 | " | Comparative Compound (f) | −0.47 | " |
| B-5 | " | Compound No. 3 | −0.39 | Invention |
| B-6 | " | Compound No. 4 | −0.38 | " |
| B-7 | M-5 | — | −1.99 | Comparison |
| B-8 | " | Comparative Compound (d) | −0.71 | " |
| B-9 | " | Comparative Compound (e) | −0.69 | " |
| B-10 | " | Comparative Compound (f) | −0.69 | " |
| B-11 | " | Compound No. 3 | −0.23 | Invention |
| B-12 | " | Compound No. 4 | −0.22 | " |
| B-13 | M-6 | — | −1.02 | Comparison |
| B-14 | " | Compound No. 1 | −0.24 | Invention |
| B-15 | " | Compound No. 12 | −0.30 | " |
| B-16 | " | Compound No. 19 | −0.29 | " |
| B-17 | M-23 | — | −1.81 | Comparison |
| B-18 | " | Compound No. 1 | −0.25 | Invention |
| B-19 | " | Compound No. 3 | −0.22 | " |
| B-20 | " | Compound No. 14 | −0.30 | " |

Comparative Compound (d):

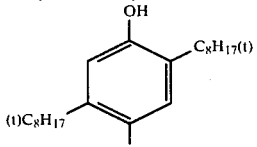

Comparative Compound (e):

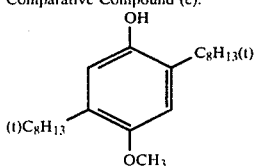

Comparative Compound (f):

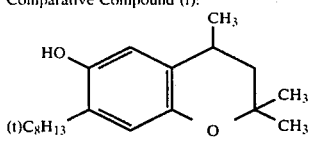

It is apparent from Table 2 that the compounds of the formula (I) according to the present invention are superior to the known decoloration preventing agents in improving the light-fastness of dye images. In addition, it can be seen that the light-fastness improving effect of the compounds of the present invention is particularly notable when using pyrazoloazole couplers of formula (XIV) according to the present invention as compared with the commonly employed 5-pyrazolone type magenta couplers.

EXAMPLE 3

On a paper support laminated with polyethylene on both sides prepared as in Example 1, the following layers were coated in the order listed, to prepare a color photographic light-sensitive material (Sample C-1).

| Layer | Component | Coverage (mg/m$^2$) |
|---|---|---|
| 1st Layer (Blue-Sensitive Layer) | Silver chlorobromide emulsion (bromide content: 80 mol %) | 400 (as Ag) |
| | Yellow coupler[1] | 300 |
| | Solvent for coupler[2] | 150 |
| | Gelatin | 1,200 |
| 2nd Layer (Intermediate Layer) | Gelatin | 1,000 |
| 3rd Layer (Green-Sensitive Layer) | Silver chlorobromide emulsion (bromide content: 70 mol %) | 200 (as Ag) |
| | Magenta coupler[3] | 300 |
| | Solvent for coupler[4] | 200 |
| | Gelatin | 1,000 |
| 4th Layer (Intermediate Layer) | Ultraviolet-absorbing agent[5] | 600 |
| | Solvent for ultraviolet-absorbing agent[6] | 300 |
| | Gelatin | 1,000 |
| 5th Layer (Red-Sensitive Layer) | Silver chlorobromide emulsion (bromide content: 50 mol %) | 300 (as Ag) |
| | Cyan coupler[7] | 400 |
| | Solvent for coupler[6] | 400 |
| | Gelatin | 1,000 |
| 6th Layer (ultraviolet Absorbing Layer) | Ultraviolet-absorbing agent[5] | 600 |
| | Solvent for ultraviolet-absorbing agent[6] | 300 |
| | Gelatin | 800 |
| 7th Layer (Protective Layer) | Gelatin | 1,000 |

Note:
[1]α-Pivaloyl-α-(2,4-dioxy-5,5'-dimethyl-oxazolidin-3-yl)-2-chloro-5-[α-(2,4-di-t-pentyloxy)butaneamido]acetanilide
[2]Dioctylbutyl phosphate
[3]1-(2,4,6-Trichlorophenyl)-3-(2-chloro-5-tetradecaneamido)anilino-4-(2-butoxy-5-t-octylphenylthio)-2-pyrazolin-5-one
[4]Tricresyl phosphate
[5]2-(2-Hydroxy-3-sec-butyl-5-t-butylphenyl)-benzotriazole
[6]Dibutyl phthalate
[7]2-[α-(2,4-Di-t-pentylphenoxy)butaneamido]-4,6-dichloro-5-methylphenol Samples C-2 to C-8 were prepared in the same manner as described above for Sample C-1 except that the decoloration preventing agent as indicated in Table 4 was added to the 3rd layer in an amount of 50 mol% based on the magenta coupler.

Each of the resulting samples was exposed to green light through a gradient wedge and subjected to development processing as shown below.

| Development Processing: | |
|---|---|
| Color Development | 3' 30" |
| Bleach-Fixing | 1' 30" |
| Washing with water | 3' |
| Drying | 10' |

The processing solution used in each step had the following formulation:

| Color Developing Solution: | |
|---|---|
| Benzyl alcohol | 15 ml |
| Diethylene glycol | 5 ml |
| Potassium carbonate | 25 g |
| Sodium chloride | 0.1 g |
| Sodium bromide | 0.5 g |
| Anhydrous sodium sulfite | 2 g |

-continued

| | |
|---|---|
| Hydroxylamine sulfate | 2 g |
| N—Ethyl-N—β-methanesulfonamidoethyl-3-methyl-4-aminoaniline sulfate | 4 g |
| Water to make | 1,000 ml (adjusted to pH 10 with NaOH) |
| Bleach-Fixing Solution: | |
| Ammonium thiosulfate | 124.5 g |
| Sodium metabisulfite | 13.3 g |
| Anhydrous sodium sulfite | 2.7 g |
| Ammonium (ethylenediaminetetraacetato)ferrate (III) | 65 g |
| Water to make | 1,000 ml (adjusted to pH 6.8) |

Each of the samples having formed thereon a magenta dye image was tested for light-fastness in a fade meter using a luminescent lamp (20,000 lux) for 4 weeks. The results obtained are shown in Table 4.

TABLE 4

| Sample No. | Dye Image Stabilizer | Change in Magenta Density (Initial Density = 1.0) | Remark |
|---|---|---|---|
| C-1 | — | −0.77 | Comparison |
| C-2 | Compound No. 1 | −0.15 | Invention |
| C-3 | Compound No. 4 | −0.12 | Comparison Invention |
| C-4 | Compound No. 14 | −0.13 | Comparison Invention |
| C-5 | Compound No. 17 | −0.16 | Comparison Invention |
| C-6 | Comparative Compound (a) | −0.22 | Comparison |
| C-7 | Comparative Compound (e) | −0.28 | Comparison |
| C-8 | Comparative Compound (c) | −0.31 | Comparison |

It can be seen from the results of Table 4 that the dye image stabilizers according to the present invention are very effective in preventing decoloration due to light in multilayer films and are superior to the known decoloration preventing agents.

EXAMPLE 4

A coating composition for a green-sensitive emulsion layer was prepared in the same manner as described for Sample A-1 in Example 1 except for using Magenta Coupler M-5 in place of Magenta Coupler (a). A multilayer sample D-1 was produced according to the formulation shown below using the resulting coating composition as the 3rd layer to a coupler coverage of 320 mg/m$^2$.

| Layer | | Coverage (mg/m$^2$) |
|---|---|---|
| Support | paper support laminated with polyethylene on both sides | |
| 1st Layer | Silver chlorobromide emulsion (bromide content: 80 mol %) | 350 (as Ag) |
| | Yellow coupler$^{(1)}$ | 500 |
| | Solvent for coupler$^{(2)}$ | 400 |
| | Gelatin | 1,500 |
| 2nd Layer | Color mixing preventing agent$^{(3)}$ | 200 |
| | Solvent$^{(4)}$ | 100 |
| | Gelatin | 1,100 |
| 3rd Layer | Silver chlorobromide emulsion (bromide content: 50 mol %) | 180 (as Ag) |
| | Magenta coupler M-5 | 320 |
| | Solvent for coupler$^{(5)}$ | 320 |
| 4th Layer | Ultraviolet-absorbing agent$^{(6)}$ | 200 |
| | Color mixing preventing agent$^{(3)}$ | 200 |
| | Solvent$^{(4)}$ | 300 |
| | Gelatin | 1,600 |
| 5th Layer | Silver chlorobromide emulsion (bromide content: 50 mol %) | 250 (as Ag) |
| | Cyan coupler$^{(7)}$ | 500 |
| | Solvent for coupler$^{(4)}$ | 250 |
| | Gelatin | 1,200 |
| 6th Layer | Ultraviolet-absorbing agent$^{(6)}$ | 360 |
| | Solvent for ultraviolet-absorbing agent$^{(4)}$ | 120 |
| | Gelatin | 1,000 |
| 7th Layer | Gelatin | 1,600 |

Note:
$^{(1)}$α-Pivaloyl-α-(2,4-dioxo-5,5'-dimethyloxazolidin-3-yl)-2-chloro-5-[α-(2,4,-di-t-pentylphenoxy)-butaneamido]acetanilide
$^{(2)}$Dioctylbutyl phosphate
$^{(3)}$2,5-Dioctylhydroquinone
$^{(4)}$Dibutyl phthalate (UV-21)
$^{(5)}$Tricresyl phosphate
$^{(6)}$2-(2-Hydroxy-3-sec-butyl-5-t-butylphenyl)benzotriazole
$^{(7)}$2-[α-(2,4-Di-t-pentylphenoxy)butaneamido]-4,6-dichloro-5-methylphenol Samples D-2, 3 and 4 were prepared in the same manner as Sample D-1 except that the 3rd layer further contained the dye image stabilizer indicated in Table 5.

Sample D-5 was produced in the same manner as Sample D-1 except that Magenta Coupler (a) as used in Example 1 was used in place of Magenta Coupler M-5 to a coupler coverage of 280 mg/m$^2$ and the silver coverage and the solvent coverage as indicated in the above-described multilayer formulation for the 3rd layer were changed to 360 mg/m$^2$ and 280 mg/m$^2$, respectively.

Sample D-6 was produced in the same manner as Sample D-5 except that the 3rd layer further contained the dye image stabilizer shown in Table 5 (Compound No. 3).

Each of the resulting samples was exposed to light and development processed in the same manner as Example 1 and tested for light-fastness in a fade meter using a luminescent lamp (15,000 lux) for 4 weeks. The change in density of the area having an initial density of 1.0 was determined, and the results are shown in Table 5.

TABLE 5

| Sample No. | Magenta Coupler | Dye Image Stabilizer | Amount of Stabilizer (mol %/Coupler) | Change of Density (Initial Density = 1.0) | Remark |
|---|---|---|---|---|---|
| D-1 | M-5 | — | — | −0.42 | Comparison |
| D-2 | " | Compound No. 3 | 50 | −0.14 | Invention |
| D-3 | " | Compound No. 3 | 100 | −0.09 | " |
| D-4 | " | Compound No. 3 + Comparative Compound (g) | 100  5 | — | " |
| D-5 | (a) | — | — | −0.33 | Comparison |

TABLE 5-continued

| Sample No. | Magenta Coupler | Dye Image Stabilizer | Amount of Stabilizer (mol %/Coupler) | Change of Density (Initial Density = 1.0) | Remark |
|---|---|---|---|---|---|
| D-6 | " | Compound No. 3 | 100 | −0.18 | " |

Comparative Compound (g)

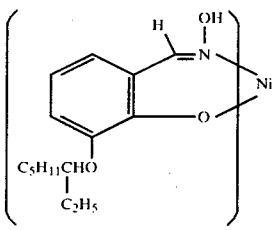

disclosed in Japanese Patent Application (OPI) No. 83162/84

From the results of Table 5, it can be seen that the dye image stabilizer according to the present invention exhibits a superior stabilizing effect on the dye images formed from the pyrazoloazole magenta coupler (M-5) of the formula (XIV) than on the dye image formed from the conventional 5-pyrazolone magenta coupler (a), and that the effect becomes more pronounced as the amount to be added increases. Further, it was proved that the dye image stabilizer according to the present invention is synergistically effective when used in combination with a known dye image stabilizer.

Separately, each of Samples D-1 to D-4 was exposed to light using blue, green and red color separation filters, and development processed in the same manner as described in Example 1. Comparison of the hue of the magenta images thus produced established that Samples D-2, 3 and 4 had a hue with excellent saturation equal to that of Sample D-1, indicating that addition of the compound of the present invention had no adverse influence on the hue developed.

EXAMPLE 5

A coating composition for a green-sensitive emulsion layer was prepared in the same manner as described in Example 1 for Sample A-1 except that Magenta Coupler M-5 was used in place of Coupler (a) and Compound No. 3 was added to the emulsified dispersion in an amount of 50 mol% based on the coupler (i.e., the same coating composition as used for Sample D-2).

Samples D-7 to D-9 were produced according to the same multilayer formulation as used in Example 4 using the above-prepared coating composition as the 3rd layer with the following exceptions:

Sample D-7: The cyan coupler used in the 5th layer was replaced by the same amount of 2-[α-(2,4-di-t-pentylphenoxy)butaneamido]-4,6-dichloro-5-ethylphenol.

Sample D-8: An equimolar mixture of the cyan coupler used in the 5th layer and 5-[2-(4-t-amyl-2-chlorophenoxy)octaneamido]-4-chloro-2-(2-chlorobenzamido)phenol was used in place of the cyan coupler as used in Example 4 to a coupler coverage of 1.1 times the coverage used in Example 4.

Sample D-9: The 1st layer further contained Compound (h) of the following formula in an amount of 20 mol% based on the yellow coupler.

Compound (h):

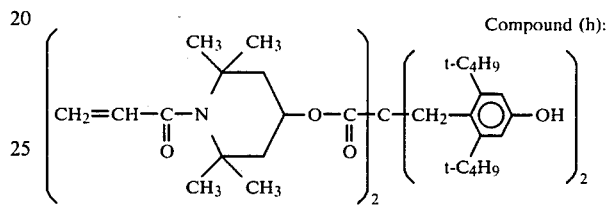

Each of the resulting samples and Samples D-1, 5 and 6 of Example 4 were exposed to light and processed in the same manner as described in Example 1 to obtain a dye image.

When the dye images thus produced were preserved at 100° C. for 7 days, or alternatively at 60° C. and at 90% RH for 6 weeks, no substantial change of magenta density was observed and the non-color image areas exhibited little staining under either condition in Samples D-7 to D-9 as shown in Table 6.

These results prove that the dye image stabilizer (I) according to the present invention is effective to stabilize magenta dye images formed from the magenta couplers represented by formula (XIV) and is also effective to prevent generation of stain in white background against heat and humidity.

Further, it was found that these effects of the stabilizer (I) are independent of the composition of the adjacent layer.

TABLE 6

| Sample No. | Change in Magenta Density* (Initial Density = 1.0) | |
|---|---|---|
| | 100° C., 7 Days | 60° C., 90% RH, 6 Weeks |
| D-1 | 0.96 (0.16) | 0.95 (0.18) |
| D-5 | 0.94 (0.38) | 0.93 (0.43) |
| D-6 | 0.96 (0.36) | 0.95 (0.40) |
| D-7 | 0.98 (0.14) | 0.97 (0.15) |
| D-8 | 0.99 (0.13) | 0.98 (0.15) |
| D-9 | 1.00 (0.13) | 0.98 (0.14) |

Note: *The value in parentheses indicate the density of the non-color area as determined through a blue filter.

While the invention has been described in detail and with reference to specific examples thereof, it will be apparent to one skilled in the art that various changes and modifications can be made therein without departing from the spirit and scope thereof.

What is claimed is:

1. A silver halide photogrpahic light-sensitive material comprising a support having thereon at least one photographic layer containing at least one compound represented by formula (I):

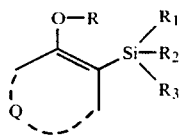

wherein R represents a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group,

a substituted or unsubstituted silyl group, a substituted or unsubstituted phosphoric acid group, or a divalent group derived from the above-described groups which forms a ring together with the oxygen atom linking to —R and the carbon atom which is in the ortho-position to —O—R and to which

is not bonded; $R_1$, $R_2$ and $R_3$ which may be the same or different each represents a hydrogen atom, a substituted or unsubstituted alkyl group, a substituted or unsubstituted alkenyl group, a substituted or unsubstituted cycloalkyl group, a substituted or unsubstituted aralkyl group, or a substituted or unsubstituted aryl group; Q represents an atomic group necessary to form a substituted or unsubstituted aromatic ring; $R_4$ represents a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted alkoxy group, a substituted or unsubstituted aryloxy group, a substituted or unsubstituted amino group, a substituted or unsubstituted cycloamino group, a substituted or unsubstituted alkylthio group, a substituted or unsubstituted arylthio group, a substituted or unsubstituted acyl group, or a substituted or unsubstituted alkoxycarbonyl group; and $R_5$ represents a H atom, substituted or unsubstituted alkyl group, a substituted or unsubstituted cycloalkyl group, a substituted or unsubstituted alkenyl group, or a substituted or unsubstituted aryl group.

2. A silver halide photographic light-sensitive material as claimed in claim 1, wherein said material further contains a pyrazoloazole coupler represented by formula (XIV):

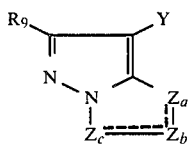

wherein $R_9$ represents a hydrogen atom, a halogen atom, a substituted or unsubstituted alkyl group, a substituted or unsubstituted aryl group, a substituted or unsubstituted heterocyclic group, a cyano group, a substituted or unsubstituted alkoxy group, a substituted or unsubstituted aryloxy group, a substituted or unsubstituted heterocyclic oxy group, a substituted or unsubstituted acyloxy group, a substituted or unsubstituted carbamoyloxy group, a substituted or unsubstituted silyloxy group, a substituted or unsubstituted sulfonyloxy group, a substituted or unsubstituted acylamino group, a substituted or unsubstituted anilino group, a substituted or unsubstituted ureido group, a substituted or unsubstituted imido group, a substituted or unsubstituted sulfamoylamino group, a substituted or unsubstituted carbamoylamino group, a substituted or unsubstituted alkylthio group, a substituted or unsubstituted arylthio group, a substituted or unsubstituted heterocyclic thio group, a substituted or unsubstituted alkoxycarbonylamino group, a substituted or unsubstituted aryloxycarbonylamino group, a substituted or unsubstituted sulfonamido group, a substituted or unsubstituted carbamoyl group, a substituted or unsubstituted acyl group, a substituted or unsubstituted sulfamoyl group, a substituted or unsubstituted sulfonyl group, a substituted or unsubstituted sulfinyl group, a substituted or unsubstituted alkoxycarbonyl group, or a substituted or unsubstituted aryloxycarbonyl group; Y represents a hydrogen atom or a group releasable upon coupling with an oxidation product of an aromatic primary amine developing agent; $Z_a$, $Z_b$ and $Z_c$ each represents a methine group, a substituted methine group, =N— or —NH—; either the $Z_a$—$Z_b$ bond or the $Z_b$—$Z_c$ bond is a double bond with the another being a single bond; provided that when $Z_b$—$Z_c$ represents a carbon-carbon double bond, $Z_b$ and $Z_c$ may form a condensed aromatic ring; and further provided that the pyrazoloazole coupler may be a polymer comprising monomer units represented by formula (XIV) and linked at $R_9$ or Y, or a polymer linked at $Z_a$, $Z_b$ or $Z_c$ when $Z_a$, $Z_b$ or $Z_c$ represents a substituted methine group.

3. A silver halide photographic light-sensitive material as claimed in claim 1, wherein the substituent for the group represented by R having at least one substituent is a halogen atom, a cyano group, a hydroxyl group, a mercapto group, a carboxyl group, a sulfoxy group, a nitro group, a carbamoyl group, an alkoxycarbonyl group, an aryloxycarbonyl group, an acyl group, an aryl group, an acyloxy group, an alkoxycarbonyloxy group, an aryloxy group, a heterocyclic oxy group, an alkoxy group, a silyloxy group, a sulfonyloxy group, a carbamoyloxy group, an acylamino group, a sulfonamido group, an alkoxycarbonylamino group, an aryloxycarbonylamino group, an imido group, an amino group, a ureido group, a sulfamoyl group, an alkylsulfonyl group, an arylsulfonyl group, an alkylsulfinyl group, an arylsulfinyl group, an alkylthio group, an arylthio group, a heterocyclic group.

4. A silver halide photographic light-sensitive material as claimed in claim 1, wherein the compound of the formula (I) is represented by formula (II), (III), (IV), (V), (VI), (VII), (VIII) or (IX):

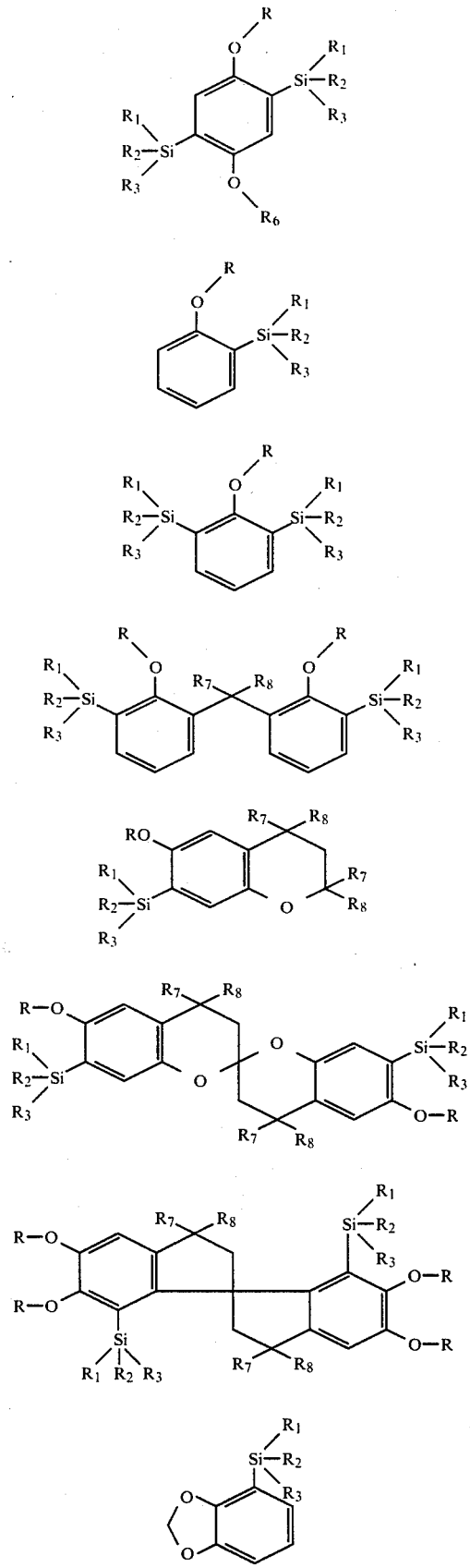

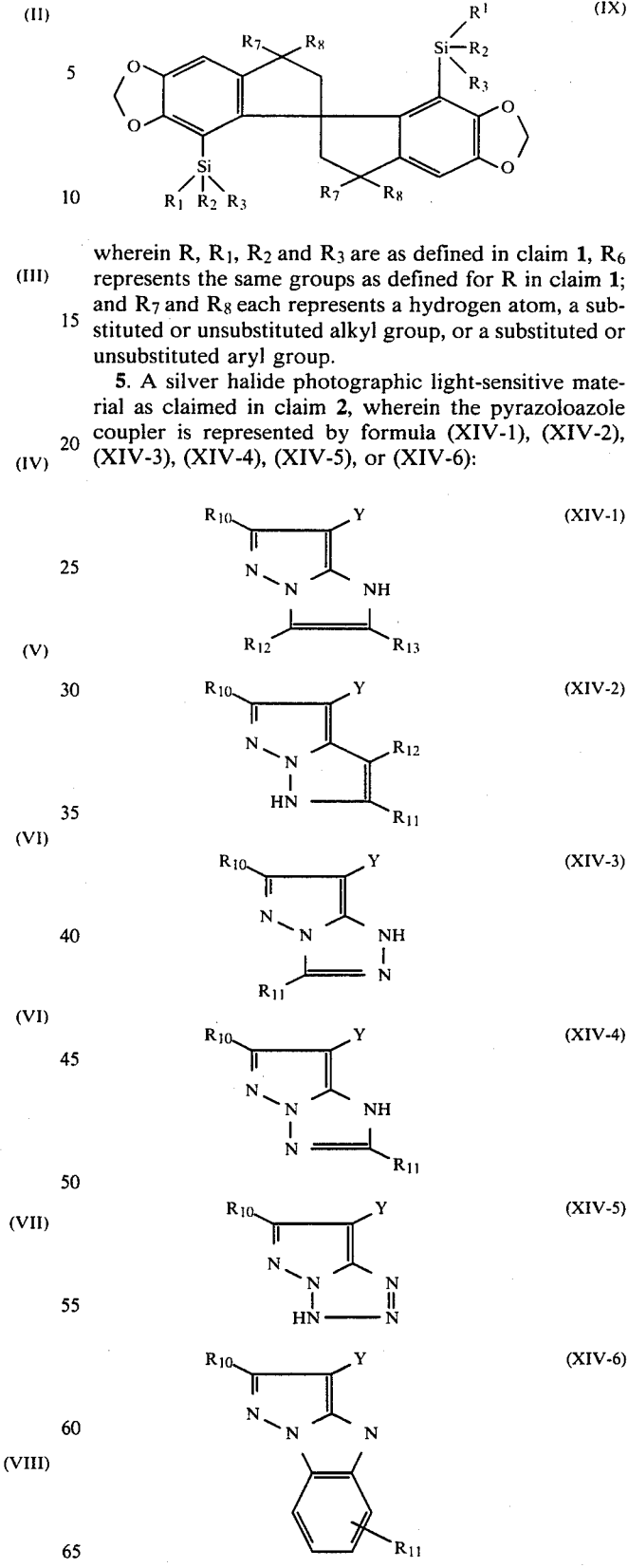

wherein R, $R_1$, $R_2$ and $R_3$ are as defined in claim 1, $R_6$ represents the same groups as defined for R in claim 1; and $R_7$ and $R_8$ each represents a hydrogen atom, a substituted or unsubstituted alkyl group, or a substituted or unsubstituted aryl group.

5. A silver halide photographic light-sensitive material as claimed in claim 2, wherein the pyrazoloazole coupler is represented by formula (XIV-1), (XIV-2), (XIV-3), (XIV-4), (XIV-5), or (XIV-6):

wherein $R_{10}$, $R_{11}$ and $R_{12}$ each represents a hydrogen atom, a halogen atom, a substituted or unsubstituted alkyl group, a substituted or unsubstituted aryl group, a substituted or unsubstituted heterocyclic group, a cyano group, a substituted or unsubstituted alkoxy group, a substituted or unsubstituted aryloxy group, a substituted or unsubstituted heterocyclic oxy group, a substituted or unsubstituted acyloxy group, a substituted or unsubstituted carbamoyloxy group, a substituted or unsubstituted silyloxy group, a substituted or unsubstituted sulfonyloxy group, a substituted or unsubstituted acylamino group, a substituted or unsubstituted anilino group, a substituted or unsubstituted ureido group, a substituted or unsubstituted imido group, a substituted or unsubstituted sulfamoylamino group, a substituted or unsubstituted carbamoylamino group, a substituted or unsubstituted alkylthio group, a substituted or unsubstituted arylthio group, a substituted or unsubstituted heterocyclic thio group, a substituted or unsubstituted alkoxycarbonylamino group, a substituted or unsubstituted aryloxycarbonylamino group, a substituted or unsubstituted sulfonamido group, a substituted or unsubstituted carbamoyl group, a substituted or unsubstituted acyl group, a substituted or unsubstituted sulfamoyl group, a substituted or unsubstituted sulfonyl group, a substituted or unsubstituted sulfinyl group, a substituted or unsubstituted alkoxycarbonyl group, or a substitited or unsubstituted aryloxycarbonyl group; a divalant group to form a bis-compund, or a single bond or a linking group by which the compound of formula (XIV-1), (XIV-2), (XIV-3), (XIV-4), (XIV-5) or (XIV-6) is boned to a vynyl group to form a vynyl monomer, and Y represents a hydrogen atom, a halogen atom, a carbonyl group, a group which is boneded to the carbon atom at the coupling position via an oxygen atom, a nitrogen atom or a sulfur atom and which is releasable upon said coupling reaction, or a divalent group to form a bis-compound.

6. A silver halide photographic light-sensitive material as claimed in claim 5, wherein the divalent group represented by $R_{10}$, $R_{11}$, $R_{12}$ or Y is a substituted or unsubstituted alkylene group, a substituted or unsubstituted phenylene group, or a —NHCO—$R_{13}$—CONH— group, wherein $R_{13}$ represents a substituted or unsubstituted alkylene group or a substituted or unsubstituted phenylene group.

7. A silver halide photographic light-sensitive material as claimed in claim 5, wherein the linking group represented by $R_{10}$, $R_{11}$ or $R_{12}$ is a substituted or unsubstituted alkylene group, a substituted or unsubstituted phenylene group, —NHCO—, —CONH—, —O—, —CO—, a substituted or unsubstituted aralkylene group or a combination thereof.

8. A silver halide photographic light-sensitive material as claimed in claim 2, wherein the pyrazoloazole coupler is a compound represented by formula (XIV-1)

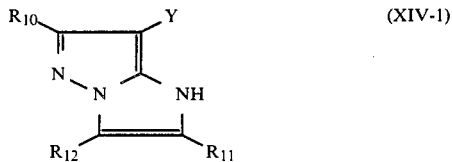

(XIV-1)

9. A silver halide photographic light-sensitive material as claimed in claim 2, wherein the pyrazoloazole coupler is a compound represented by formula (XIV-4)

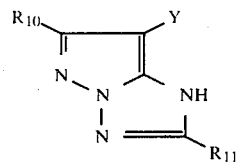

10. A silver halide photographic light-sensitive material as claimed in claim 1, wherein the compound of formula (I) is present in an amount of from about $1 \times 10^{-5}$ to 1 mol per mole of silver halide.

11. A silver halide photographic light-sensitive material as claimed in claim 1, wherein the compound of formula (I) is present in an amount of from about $1 \times 10^{-3}$ to $5 \times 10^{-1}$ mol per mole of silver halide.

12. A silver halide photographic light-sensitive material as claimed in claim 2, wherein the coupler of formula (XIV) is present in an amount of from about $2 \times 10^{-3}$ to $5 \times 10^{-1}$ mol per mole of silver.

13. A silver halide photographic light-sensitive material as claimed in claim 2, wherein said coupler of formula (XIV) is present in an amount of from about $1 \times 10^{-2}$ to $5 \times 10^{-1}$ mol per mole of silver.

14. A silver halide photographic light-sensitive material as claimed in claim 2, wherein the material contains the compound of the formula (I) and the coupler of the formula (XIV) in the same photographic layer.

15. A ailver halide photographic light-sensitive material as claimed in claim 1, wherein the photographic leyer containing the compound represented by formula (I) is a silver halide light-sensitive emulsion layer.

16. A silver halide photographic light-sensitive material as claimed claim 1, wherein the photographic layer containing the compound represented by formula (I) is a light-insensitive photographic auxiliary layer.

17. A silver halide photographic light-sensitive material as claimed in claim 16, wherein the compound represented by formula (I) is contained in an amount of from about $3 \times 10^{-6}$ to $3 \times 10^{-1}$ mol /m² in the light-insensitive photographic auxiliary layer.

18. A silver halide photographic light-sensitive material as claimed in claim 16, wherein the compound by formula (I) is contained in an amount of from about $3 \times 10^{-3}$ to $1.5 \times 10^{-1}$ mol/m² in the light-insensitive photographic auxiliary layer.

19. A silver halide photographic light-sensitive material as claimed in claim 5, wherein the substituent for the group represented by $R_{10}$, $R_{11}$ and $R_{12}$ having at least one substituent is a hydrogen atom, a halogen atom, an alkyl group, an aryl group, a heterocyclic group, a cyano group, an alkoxy group, an aryloxy group, a heterocyclic oxy group, a silyloxy group, a sulfonyloxy group, an acylamino group, a ureido group, a sulfamonylamino group, a carbamoylamino group, an alkylthio group, an arylthio group, a heterocyclic thio group, an alkoxycarbonylamino group, an aryloxycarbonylamino group, a sulfonamido group, a carbamonyl group, an acyl group, a sulfamoyl group, a sulfonyl group, a sulfinyl group, an alkoxycarbonyl group, and aryloxycarbonyl group.

* * * * *